United States Patent [19]
Tamano et al.

[11] Patent Number: 6,150,042
[45] Date of Patent: *Nov. 21, 2000

[54] MATERIAL FOR ORGANOELECTRO-LUMINESCENCE DEVICE AND USE THEREOF

[75] Inventors: Michiko Tamano; Toshio Enokida; Toshikazu Onikubo; Satoshi Okutsu, all of Tokyo, Japan

[73] Assignee: Toyo Ink Manufacturing Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/986,788

[22] Filed: Dec. 8, 1997

[30] Foreign Application Priority Data

| Dec. 9, 1996 | [JP] | Japan | 8-328069 |
| Apr. 7, 1997 | [JP] | Japan | 9087802- |
| Apr. 21, 1997 | [JP] | Japan | 9-102863 |
| Apr. 21, 1997 | [JP] | Japan | 9-102866 |

[51] Int. Cl.$^7$ .................................................. H05B 33/12
[52] U.S. Cl. .................... 428/690; 428/917; 428/704; 428/332; 313/504; 313/506
[58] Field of Search .................... 428/690, 691, 428/917, 704, 332; 313/504–509

[56] References Cited

U.S. PATENT DOCUMENTS 5,736,068  4/1998  Haeuseling et al. ............ 252/299.62

FOREIGN PATENT DOCUMENTS

| 0 742 197 | 11/1996 | European Pat. Off. . |
| WO 95/14652 | 6/1995 | WIPO . |
| WO 95/17018 | 7/1995 | WIPO . |
| WO 96/00208 | 1/1996 | WIPO . |

OTHER PUBLICATIONS

Boden et al., "Mechanism of charge transport is discotic liquid crystals", *Physical Review, B. Condensed Matter*, vol. 52, No. 18, Nov. 1, 1995, pp. 13274–13280.

van de Craats et al., "The Mobility of Charge Carriers in All Four Phases of the Columnar Discotic Material Hexakis(hexylthio)triphenylene: Combined TOF and PR-TRMC Results", *Advanced Materials*, vol. 8, No. 10, Oct., 1996, pp. 823–826.

Kreuder et al., "The Wheel of Mainz as a liquid crystal?—Structural variation and mesophase properties of trimeric discotic compounds", *Agnew. Chem. Int. Edn. Engl.*, vol. 12, 1987, pp. 1249–1252. (No Month).

Breslow et al., "Ground state pi–electron triplet molecules of potential use in the synthesis of organic ferromagnets", *Tetrahedron*, vol. 38, No. 6, 1982, pp. 863–867. (No Month).

Chapuzet et al., "The anodic trimerization of aromatic orthodiethers: New developments", *Tetrahedron*, vol. 47, No. 4/5, 1991, pp. 791–795. No Month).

Chapuzet et al., "A versatile anodic source of triphenylenes possessing at least one ionophoric site", *Tetrahedron Letters*, vol. 32, No. 50, 1991, pp. 7405–7408. (No Month).

Bacher et al., "Triphenylenes: a new class of hole transport material in organic light emitting diodes" in Organic Light–Emitting Materials and Devices, Zakya H. Kafafi, Editor, Proceedings of SPIE vol. 3148, pp. 313–320 (SPIE Proceedings, Jul. 30–Aug. 1, 1997, San Diego, California).

*Primary Examiner*—Marie Yamnitzky
*Attorney, Agent, or Firm*—Wenderoth, Lind & Ponack, L.L.P.

[57] ABSTRACT

A hole-injecting material for an organic EL device, having excellent hole-injecting capability and durability and having the formula [I], [II] or [III] specified in claim 1, and an organic electroluminescence device obtained by forming either a light-emitting layer or a plurality of organic compound thin layers including the light-emitting layer between a pair of electrodes composed of a cathode and an anode, wherein at least one layer contains the above material.

8 Claims, No Drawings

MATERIAL FOR ORGANOELECTRO-LUMINESCENCE DEVICE AND USE THEREOF

FIELD OF THE INVENTION

The present invention relates to a material having a triphenylene structure, used for the production of an electroluminescence device, and an organoelectroluminscence device (to be sometimes referred to as "EL device" hereinafter) which uses the above material and is useful as a planar light source or display.

PRIOR ART

Organic photo-conductive materials are advantageously less expensive, easily processible and free from causing pollution, and a variety of compounds have been proposed. Examples of the disclosed organic photo-conductive materials include oxadiazole derivatives (U.S. Pat. No. 3,189,447), oxazole derivatives (U.S. Pat. No. 3,257,203), hydrazone derivatives (U.S. Pat. No. 3,717,462, JP-A-54-59,143, U.S. Pat. No. 4,150,978), triaryl pyrazoline derivatives (U.S. Pat. No. 3,820,989, JP-A-51-93,224, JP-A-55-108,667), arylamine derivatives (U.S. Pat. No. 3,180,730, U.S. Pat. No. 4,232,103, JP-A-55-144,250, JP-A-56-119,132), and stilbene derivatives (JP-A-58-190,953, JP-A-59-195,658).

An organic EL device is one technical example to which the hole transporting capability of an organic photo-conductive material is adapted. An EL device using an organic substance is greatly expected to be usable as a solid light-emitting inexpensive large-screen, full-color display device, and developments thereof are being made in many ways. Generally, an organic EL device is composed of a light-emitting layer and a pair of mutually opposite electrodes sandwiching the light-emitting layer. The light emission by an EL device is the following phenomenon. When an electric field is applied between the two electrodes, the cathode injects electrons into the light-emitting layer, and the anode injects holes into the light-emitting layer. Further, when the electrons recombine with the holes in the light-emitting layer, their energy level shifts from a conduction band back to a valence electron band to release energy as fluorescent light.

As compared with inorganic EL devices, conventional organic EL devices require high voltage for its activation, and further, their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect to emit light at a low voltage as low as less than 10 V, and it attracts attention (Appl. Phy. Lett., Vol. 51, page 913, 1987). The above organic EL device has a fluorescent layer containing a metal chelate complex and a hole-injecting layer containing an amine-based compound, and emits green light having a high brightness. The above organic EL device achieves a maximum brightness of 10,000 cd/m$^2$ and a maximum light emission efficiency of 1.5 lm/W at a direct current voltage of 6 or 7V and thus has nearly practically usable performance.

An organic EL device has a structure in which a light-emitting layer containing an organic fluorescent compound is provided between a metal cathode layer and a transparent anode layer. Further, an electron-injecting layer and a hole-injecting layer are provided for obtaining light emission having a high brightness at a low voltage. In the organic EL device, electrons injected from a cathode and holes injected from an anode are recombined to generate excitons and the excitons radiate light in the process of radiation thereof to be deactivated (JP-A-59-194393, JP-A-63-295695). However, when the device continues to emit light in the continuous operation under the application of direct current for a long period of time, the organic compound, or an organic photo-conductive material in particular, is promoted in crystallization, and leak current is liable to occur in the device so that the device is liable to be eventually broken. For overcoming the above problem, a compound such as 4,4',4"-tris(N,N'-diphenylamino)tiphenylamine or 4,4',4"-tris[N-(3-methylphenyl)-N-phneylamino]-triphenylamine is used as a hole-injecting material for use in a hole-injecting layer (JP-A-4-308688). The above compounds are less crystallizable owing to their steric coordination structure and are excellent in thin film formability, while they are not yet satisfactory as an organic thin film which is to constitute an organic EL device. That is, these compounds do not much undergo crystallization immediately after a film is formed therefrom, while they undergo crystallization with the passage of time and are not feasible for practical use. The device therefore easily deteriorates in the repeated use for light emission.

As discussed above, the organic EL devices which have been so far developed are not sufficient in light emission brightness and light emission stability in the repeated use for light emission. It is therefore desired to develop a hole-injecting material having excellent hole-injecting capability and durability for attaining an organic EL device having a higher light emission brightness, a high light emission efficiency and excellent stability in the repeated use for light emission.

SUMMARY OF THE INVENTION

It is an object of the present invention to provide a hole-injecting material for an organic EL device, which material has excellent hole-injecting capability and durability, and an organic EL device having a high light emission efficiency and being capable of light emission in repeated and continuous emission of light due to the use of the above hole-injecting material.

According to the present invention, there is provided a material for an organic electroluminescence device, having the formula [I], [II] or [III],

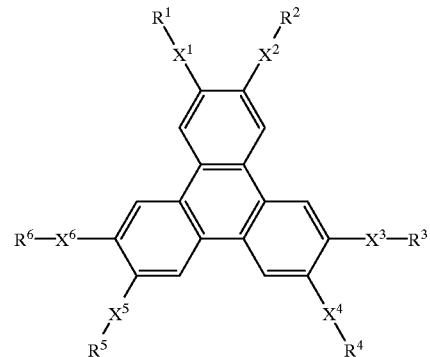

[I]

wherein each of $R^1$ to $R^6$ is independently a non-substituted alkyl group, a substituted alkyl group, a non-substituted aryl group, a substituted aryl group, a non-substituted alicyclic group, a substituted alicyclic group, a non-substituted heterocyclic group or a substituted heterocyclic group, or at least one combination of adjacent $X^1$—$R^1$ and $X^2$—$R^2$, $X^3$—$R^3$ and $X^4$—$R^4$ or $X^5$—$R^5$ and $X^6$—$R^6$ is a non-substituted monohetero-cyclic ring, a substituted mono-hetero-cyclic ring, a non-substituted fused poly-hetero-cyclic ring or a substituted fused poly-hetero-cyclic ring, and each of $X^1$ to $x^6$ is independently an oxygen atom or a sulfur atom, or each of $X^1$ to $x^6$ is independently a nitrogen atom to which a hydrogen atom, an alkyl group or an aryl group may be bonding,

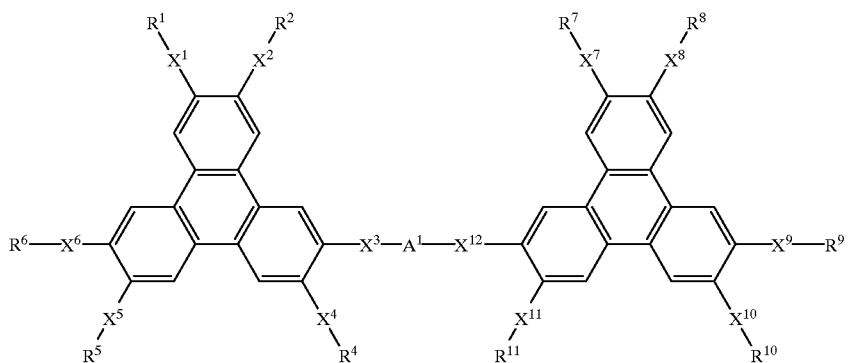

wherein each of $R^1$, $R^2$ and $R^4$ to $R^{11}$ is independently a non-substituted alkyl group, a substituted alkyl group, a non-substituted aryl group, a substituted aryl group, a non-substituted alicyclic group, a substituted alicyclic group, a non-substituted heterocyclic group or a substituted heterocyclic group, or at least one combination of adjacent $X^1$—$R^1$ and $X^2$—$R^2$, $X^5$—$R^5$ and $X^6$—$R^6$, $X^7$—$R^7$ and $X^8$—$R^8$, or $X^9$—$R^9$ and $X^{10}$—$R^{10}$ is a non-substituted mono-hetero-cyclic ring, a substituted mono-hetero-cyclic ring, a non-substituted fused poly-hetero-cyclic ring or a substituted fused poly-hetero-cyclic ring, each of $X^1$ to $X^{11}$ is independently an oxygen atom, a sulfur atom or a nitrogen atom to which a hydrgeon atom, an alkyl group or an aryl group may be bonding, and $A^1$ is a chemically rational organic residue which is composed of C, H and O, or is composed of C, H, O and S, and has a molecular weight of 500 or less,

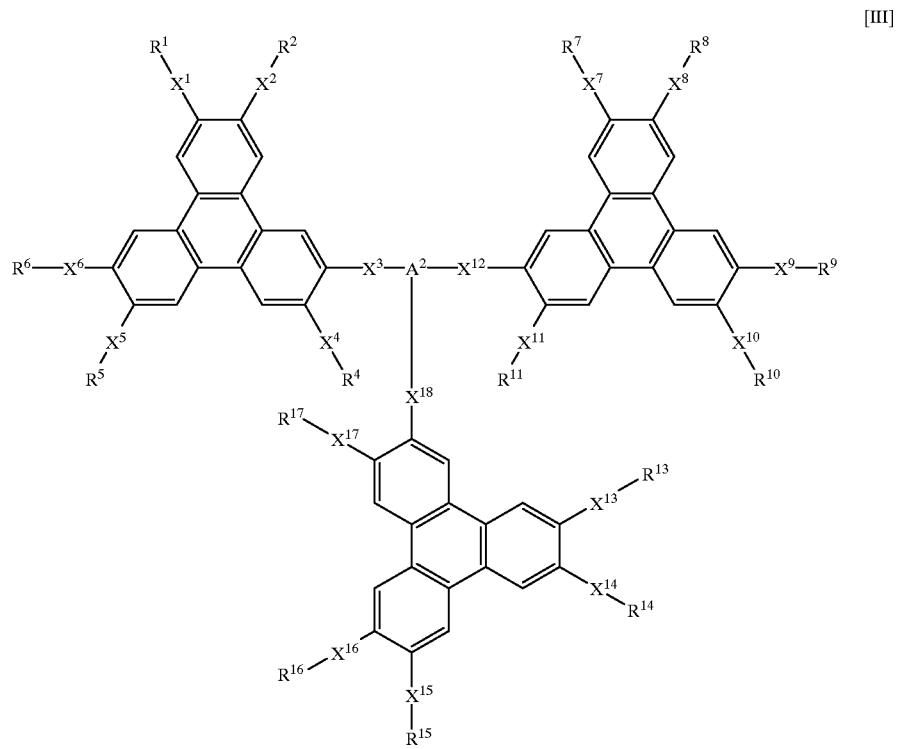

wherein each of $R^1$, $R^2$, $R^4$ to $R^{11}$ and $R^{13}$ to $R^{17}$ is independently a non-substituted alkyl group, a substituted alkyl group, a non-substituted aryl group, a substituted aryl group, a non-substituted alicyclic group, a substituted alicyclic group, a non-substituted heterocyclic group or a substituted heterocyclic group, or at least one combination of adjacent $X^1$—$R^1$ and $X^2$—$R^2$, $X^5$—$R^5$ and $X^6$—$R^6$, $X^7$—$R^7$ and $X^8$—$R^8$, $X^9$—$R^9$ and $X^{10}$—$R^{10}$, $X^{13}$—$R^{13}$ and $X^{14}$—$R^{14}$, $X^{15}$—$R^{15}$ and $X^{16}$—$R^{16}$ is a non-substituted mono-hetero-cyclic ring, a substituted mono-hetero-cyclic ring, a non-substituted fused poly-hetero-cyclic ring or a substituted fused poly-hetero-cyclic ring, each of $X^1$ to $X^{18}$ is independently an oxygen atom, a sulfur atom or a nitrogen atom to which a hydrogen atom, an alkyl group or an aryl group may be bonding, and $A^2$ is a chemically rational organic residue which is composed of C, H and O, or is composed of C, H, O and S, and has a molecular weight of 500 or less.

According to the present invention, further, there is provided an organic electroluminescence device obtained by forming either a light-emitting layer or a plurality of organic compound thin layers including the light-emitting layer between a pair of electrodes composed of a cathode and an anode, wherein at least one layer contains the above material for an organic electroluminescence device.

In a preferred embodiment of the present invention, further, the organic EL device has at least one layer containing the above material in a hole-injecting zone between the light-emitting layer and the anode.

In a preferred embodiment of the present invention, further, the light-emitting layer of the organic EL device contains the above material.

In a preferred embodiment of the present invention, further, the light-emitting layer and at least one other layer contain the above material.

In a preferred embodiment of the present invention, further, a layer containing the above material further contains an organic fluorescence dyestuff.

DETAILED DESCRIPTION OF THE INVENTION

The present inventors have made diligent studies to overcome the above problems, and have found that the hole-injecting material of the formula (1) has high hole-injecting capability and gives an organic EL device having excellent device characteristics, an excellent light emission life.

In the formula (I), each of $R^1$ to $R^6$ is independently a non-substituted alkyl group, a substituted alkyl group, a non-substituted aryl group, a substituted aryl group, a non-substituted alicyclic group, a substituted alicyclic group, a non-substituted heterocyclic group or a substituted heterocyclic group.

Examples of the substituted or non-substituted alkyl group include linear or branched alkyl groups having 1 to 18 carbon atoms such as methyl, ethyl, propyl, butyl, sec-butyl, tert-butyl, pentyl, hexyl, heptyl, octyl, stearyl, trichloromethyl, trifluoromethyl, benzyl and 2,2-dimethylbenzyl.

Examples of the substituted or non-substituted aryl group include phenyl, tolyl, naphthyl, anthranyl, phenanthrenyl, fluorenyl, acenaphthyl, azurenyl, heptanlenyl, acenaphthylenyl, pyrenyl, biphenyl, 4-ethylbiphenyl, terphenyl, quaterphenyl, benz[a]anthranyl, triphenylenyl, 2,3-benzfluorenyl and 3,4-benzpyrenyl.

Examples of the substituted or non-substituted alicyclic group include cyclopropyl, cyclobutyl, cyclopentyl, cyclohexyl, cycloheptyl cyclooctyl, 1,3-cyclohexadienyl, 2-cyclopenten-1-yl, and 2,4-cyclopentadien-1-ylidenyl.

Examples of the substituted or non-substituted heterocyclic group include thienyl, furyl, pyrrolyl, inidazolyl, pyrazolyl, pyridyl, pyrazinyl, pyrimidinyl, pyridazinyl, indolyl, quinolyl, isoquinolyl, phthalazinyl, quinoxalinyl, quinazolinyl, carbazolyl, acridinyl, phenazinyl, furfuryl, isothiazolyl, isoxasolyl, furazanyl, phenoxazinyl, benzothiazolyl, benzooxasolyl, benzimidazolyl, 2-methylpyridyl, 3-cyanopyridyl, oxazolyl, thiazolyl, imidazolyl, oxadiazolyl, thiadiazolyl and imidadiazolyl.

Typical examples of the substituent on the alkyl group, the aryl group, the alicyclic group or the heterocyclic group include halogen atoms such as fluorine, chlorine, bromine and iodine, nitro, cyano, carbonyl, hydroxyl, mercapto, substituted or non-substituted alkyl groups such as methyl, ethyl, propyl, butyl, sec-butyl, tert-butyl, pentyl, hexyl, heptyl, octyl, stearyl, trichloromethyl, trifluoromethyl, cyclopropyl, cyclohexyl, 1,3-cyclohexadienyl, 2-cyclopenten-1-yl and 2,4-cyclopentadien-1-ylidenyl, substituted or non-substituted alkoxy groups such as methoxy, ethoxy, propoxy, n-butoxy, sec-butoxy, tert-tuboxy, pentyloxy, hexyloxy, stearyloxy and trifluoromethoxy, substituted or non-substituted thioalkoxy groups such as methylthio, ethylthio, propylthio, butylthio, sec-butylthio, tert-butylthio, pentylthio, hexylthio, heptylthio and octylthio, mono- or di-substituted amino groups such as methylamino, dimethylamino, ethylamino, dipropylamino, dibutylamino, diphenylamino, bis(acetoxymethyl)amino, bis(acetoxyethyl)amino, bis(acetoxypropyl)amino, bis(acetoxybutyl)amino and dibenzylamino, substituted or non-substituted aryloxy groups such as phenoxy, p-tert-butylphenoxy and 3-fluorophenoxy, substituted or non-substituted arylthio groups such as phenylthio and 3-fluorophenylthio, substituted or non-substituted aryl groups such as phenyl, biphenyl, triphenyl, terphenyl, 3-nitrophenyl, 4-methylthiophenyl, 3,5-dicyanophenyl, o-, m- and p-tolyl, xylyl, o-, m- and p-cumenyl, mesityl, pentalenyl, indenyl, naphthyl, azulenyl, heptalenyl, acenaphthylenyl, phenalenyl, fluorenyl, anthryl, anthraquinolyl, 3-methylanthryl, phenanthryl, tirphenylenyl, pyrenyl, chrysenyl, 2-ethyl-1-chrysenyl, picenyl, perylenyl, 6-chloroperylenyl, pentaphenyl, pentacenyl, tetraphenylenyl, hexapenyl, hexacenyl, rubicenyl, coronenyl, trinaphthylenyl, heptaphenyl, heptacenyl, pyranthrenyl and ovelenyl, and substituted or non-substituted heterocylic groups such as thienyl, furyl, pyrrolyl, imidazolyl, pyrazolyl, pyridyl, pyrazinyl, pyrimidinyl, pyridazinyl, indolyl, quinolyl, isoquinolyl, phthalazinyl, quinoxalinyl, quinazolinyl, carbazolyl, acridinyl, phenazinyl, furfuryl, isothiazolyl, isoxasolyl, furazanyl, phenoxazinyl, benzothiazolyl, benzooxasolyl, benzimidazolyl, 2-methylpyridyl, 3-cyanopyridyl, oxazolyl, thiazolyl, imidazolyl, oxadiazolyl, thiadiazolyl, imidadiazolyl, carbozolyl and indolyl.

In the formula (I), each of $X^1$ to $x^6$ is independently an oxygen atom, a sulfur atom or a nitrogen atom to which a hydrogen atom, an alkyl group or an aryl group may be bonding. Examples of the alkyl group and the aryl group include those specified with regard to $R^1$ to $R^6$.

In the formula (1), alternatively, at least one combination of $X^1$—$R^1$ and $X^2$—$R^2$, $X^3$—$R^3$ and $X^4$—$R^4$ or $X^5$—$R^5$ and $X^6$—$R^6$ may form a non-substituted mono-hetero-cyclic ring, a substituted mono-hetero-cyclic ring, a non-substituted fused poly-hetero-cyclic ring or a substituted fused poly-hetero-cyclic ring.

Examples of the mono-hetero-cyclic ring or the fused poly-hetero-cyclic ring include crown ether rings such as 12-crown ring, 15-crown ring and 18-crown ring, indolyl ring, quinolyl ring, isoquinolyl ring, quinoxalinyl ring, quinazolinyl ring, carbazolinyl ring, phenazinyl ring, furfuryl ring, isothiazolyl ring, benzimidazolyl ring, 1-tetralinyl ring and 2-tetralinyl ring.

Examples of the substituent which may be substituted on the above ring include those specified with regard to $R^1$ to $R^6$.

Table 1 shows specific examples of the compound of the formula (I), while the compound of the formula (I) shall not be limited thereto.

TABLE 1

| No. | Chemical structure |
|---|---|
| 1 | 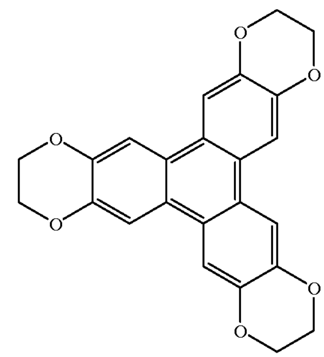 |
| 2 | 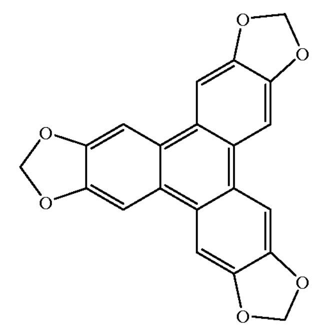 |
| 3 | 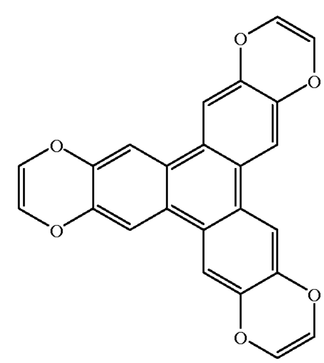 |

TABLE 1-continued
| No. | Chemical structure |
|---|---|
| 4 | 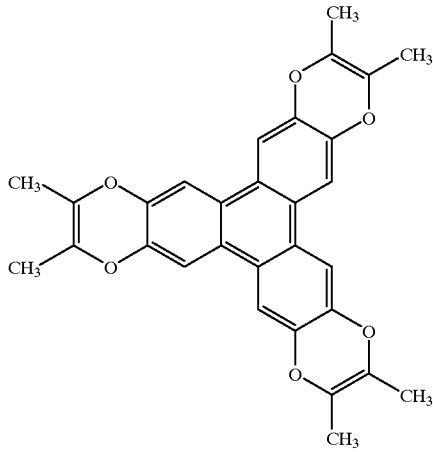 |
| 5 | 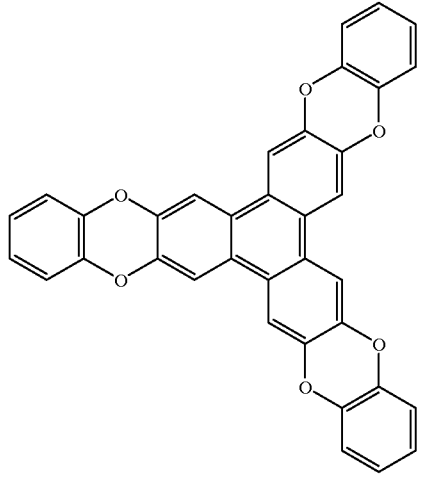 |
| 6 | 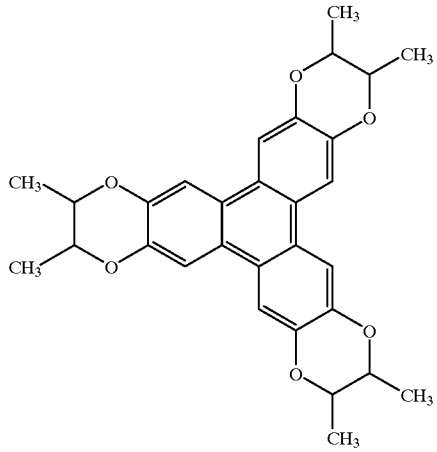 |

TABLE 1-continued
| No. | Chemical structure |
| --- | --- |
| 7 | 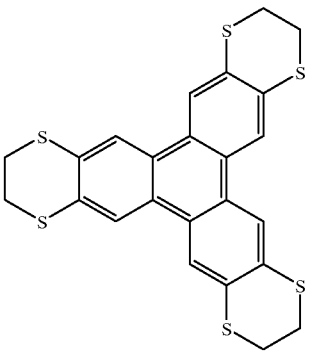 |
| 8 | 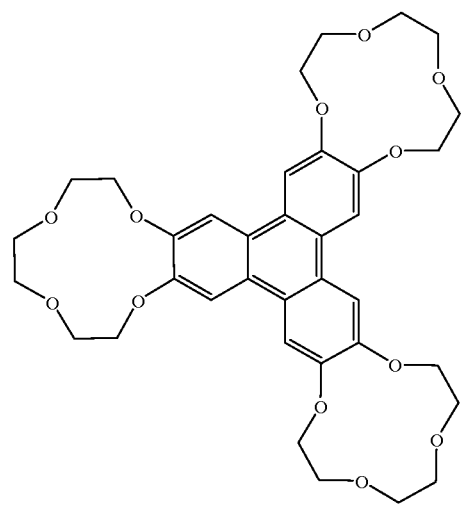 |
| 9 | 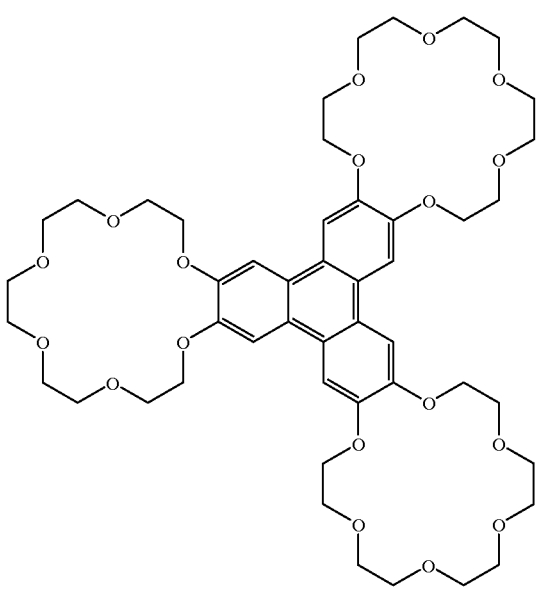 |

TABLE 1-continued

| No. | Chemical structure |
| --- | --- |
| 10 | 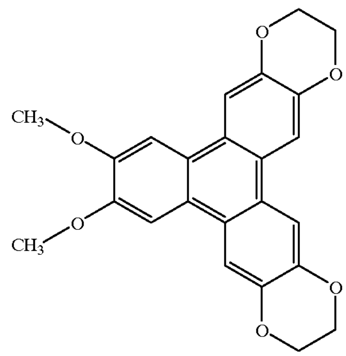 |
| 11 | 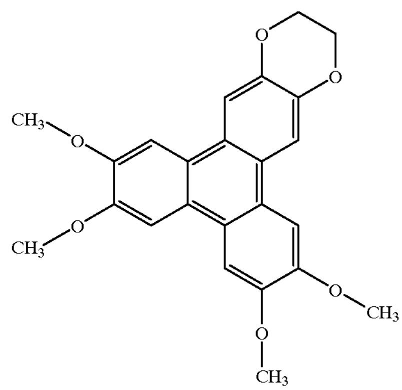 |
| 12 | 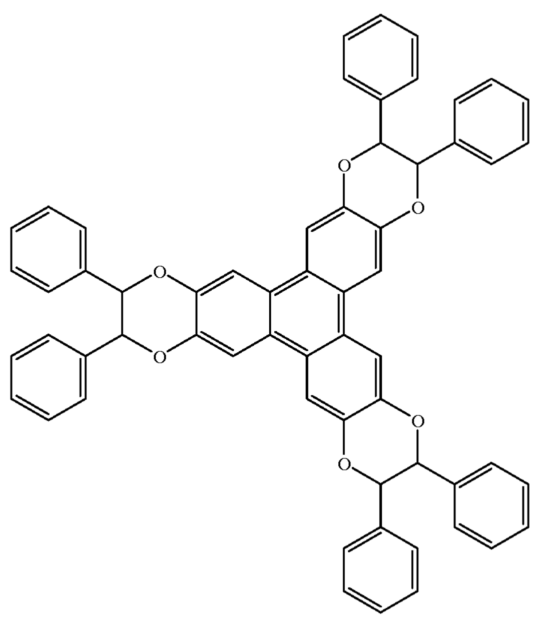 |

TABLE 1-continued

| No. | Chemical structure |
|---|---|
| 13 | 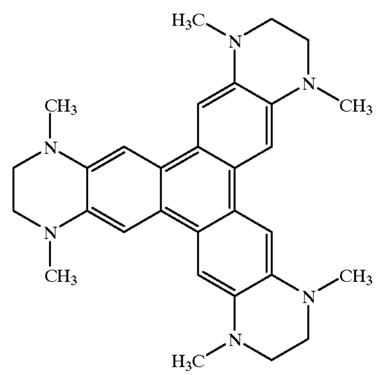 |
| 14 | 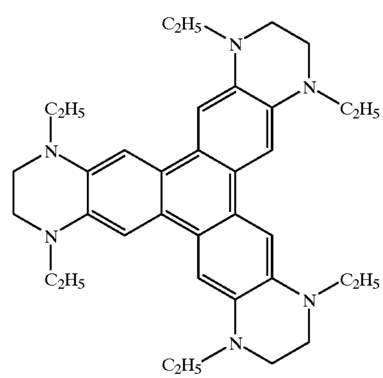 |
| 15 | 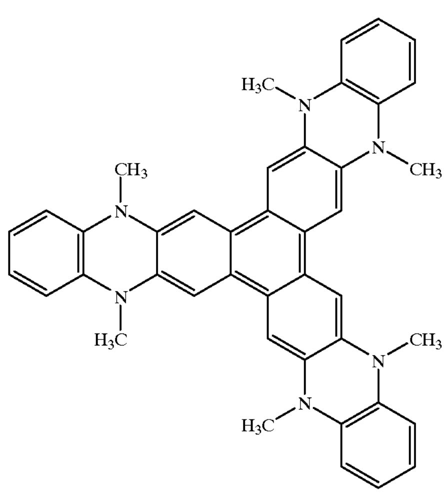 |

TABLE 1-continued
| No. | Chemical structure |
| --- | --- |
| 16 | 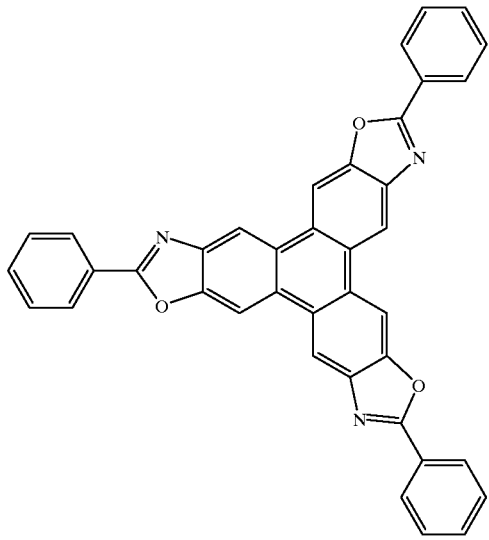 |
| 17 | 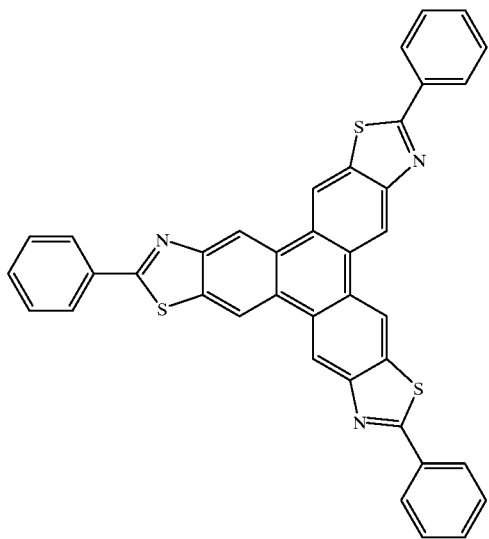 |
| 18 | 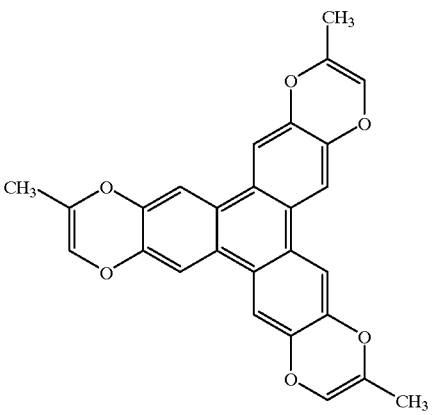 |

TABLE 1-continued
| No. | Chemical structure |
|---|---|
| 19 | 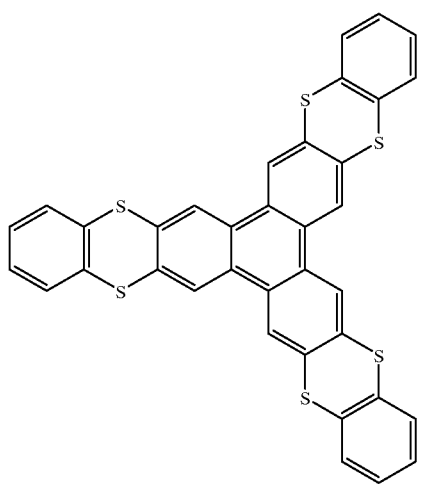 |
| 20 | 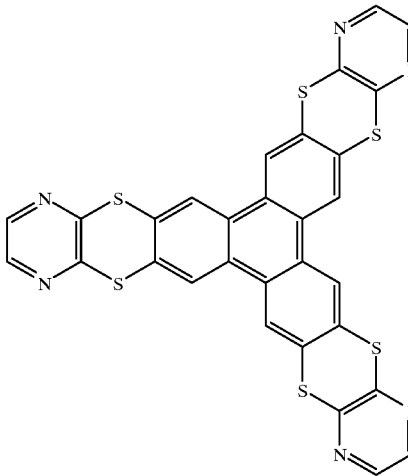 |
| 21 | 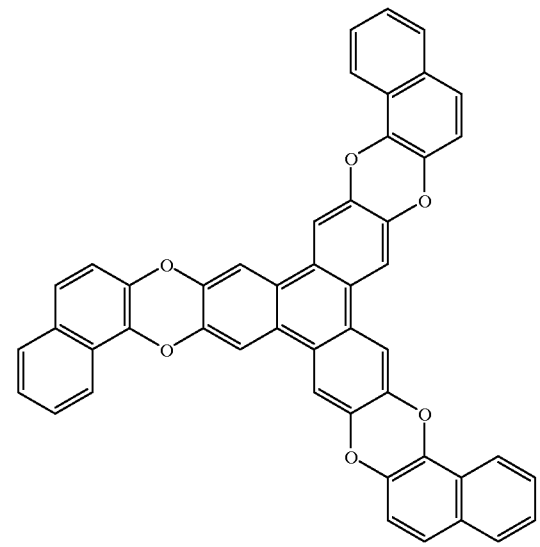 |

TABLE 1-continued
| No. | Chemical structure |
|---|---|
| 22 | 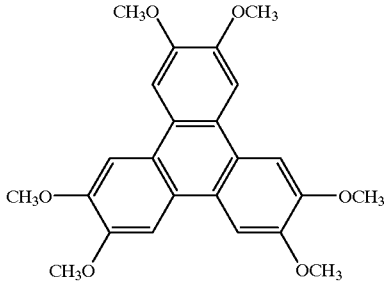 |
| 23 | 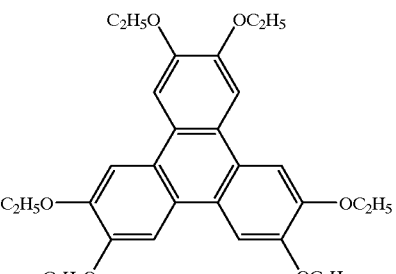 |
| 24 | 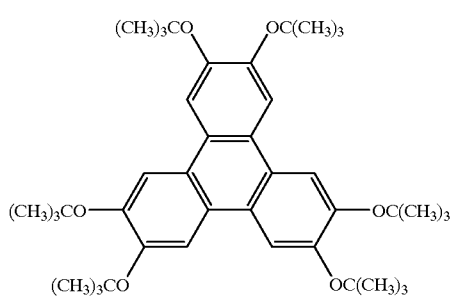 |
| 25 | 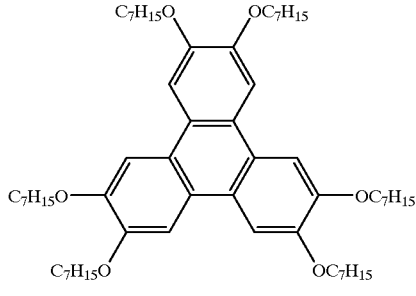 |
| 26 | 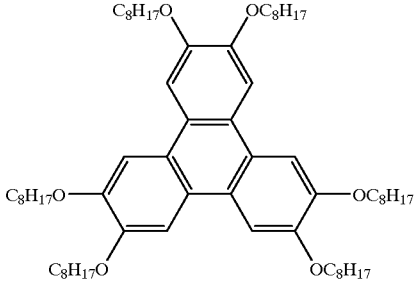 |

TABLE 1-continued
| No. | Chemical structure |
| --- | --- |
| 27 | 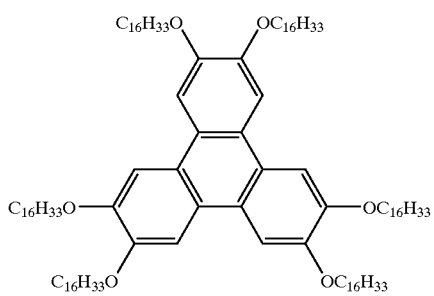 |
| 28 | 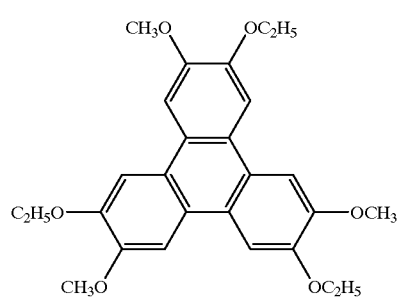 |
| 29 | 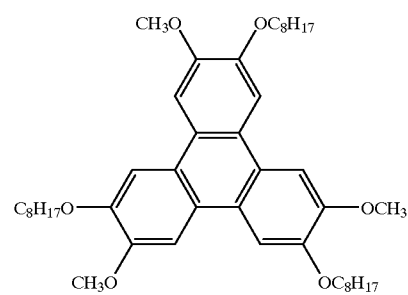 |
| 30 | 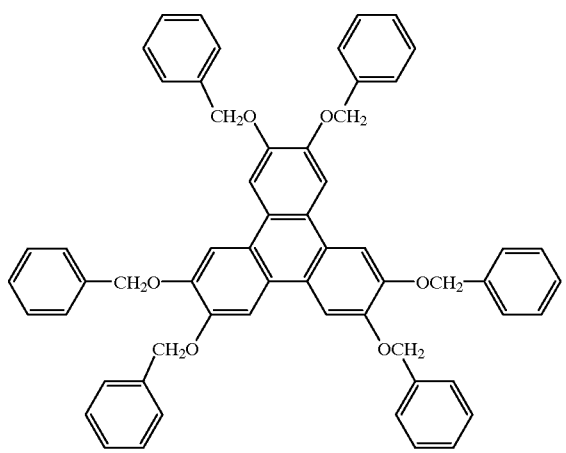 |

TABLE 1-continued
| No. | Chemical structure |
|---|---|
| 31 | 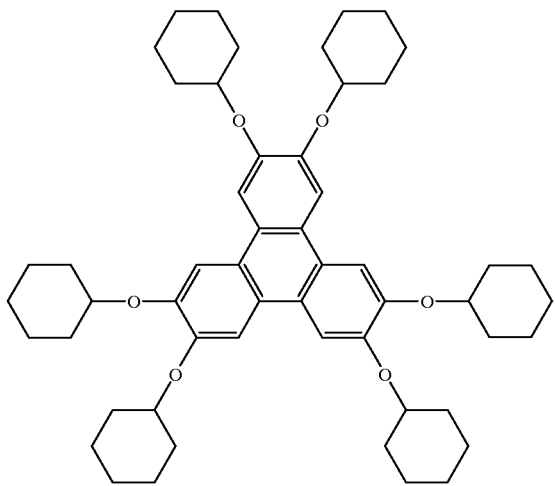 |
| 32 | 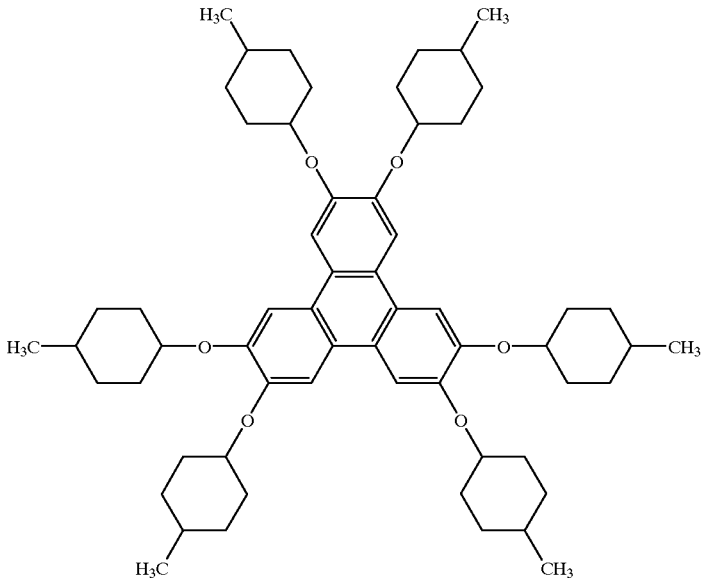 |
| 33 | 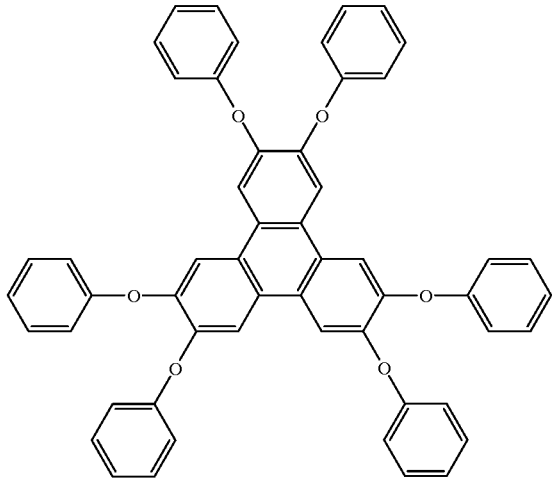 |

TABLE 1-continued
| No. | Chemical structure |
|---|---|
| 34 | 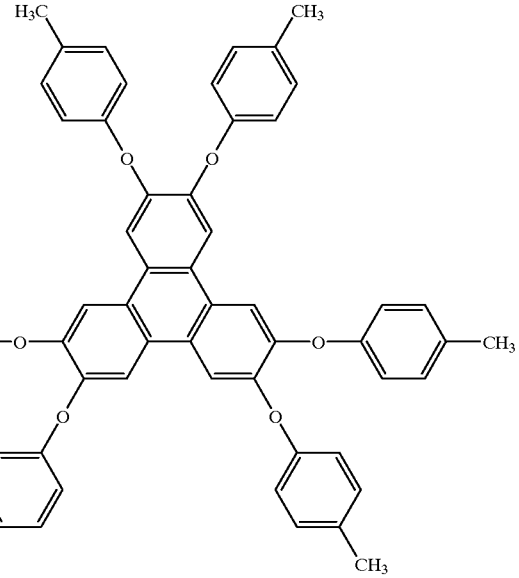 |
| 35 | 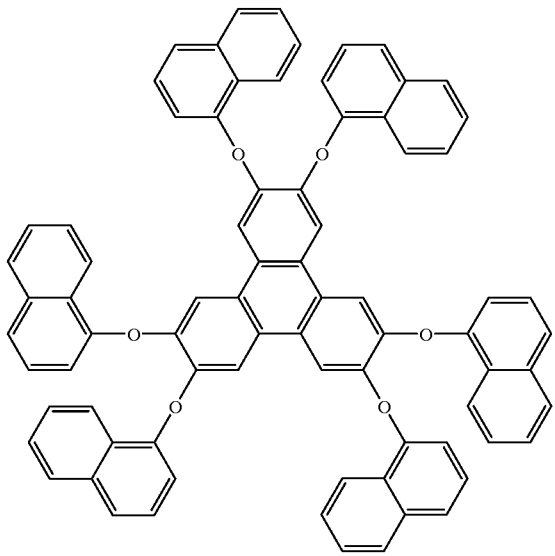 |

TABLE 1-continued
| No. | Chemical structure |
|---|---|
| 36 | 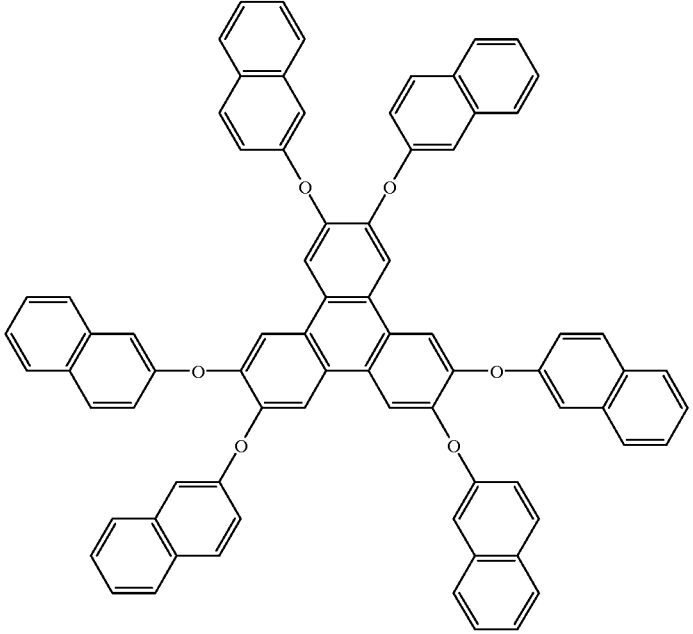 |
| 37 | 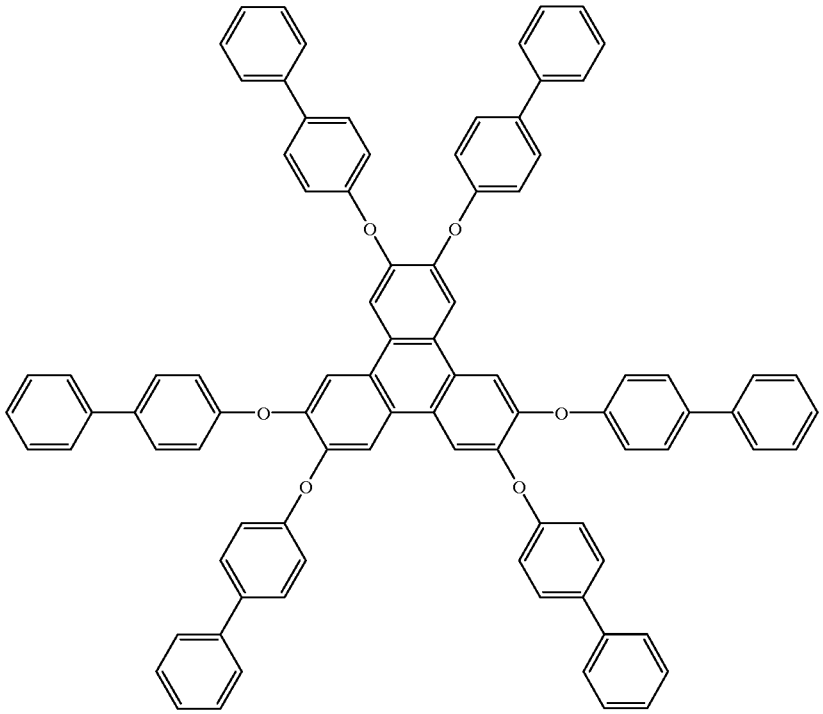 |

TABLE 1-continued
| No. | Chemical structure |
| --- | --- |
| 38 | 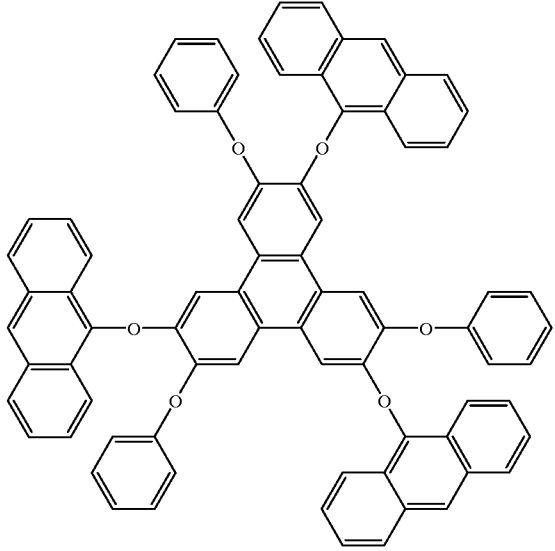 |
| 39 | 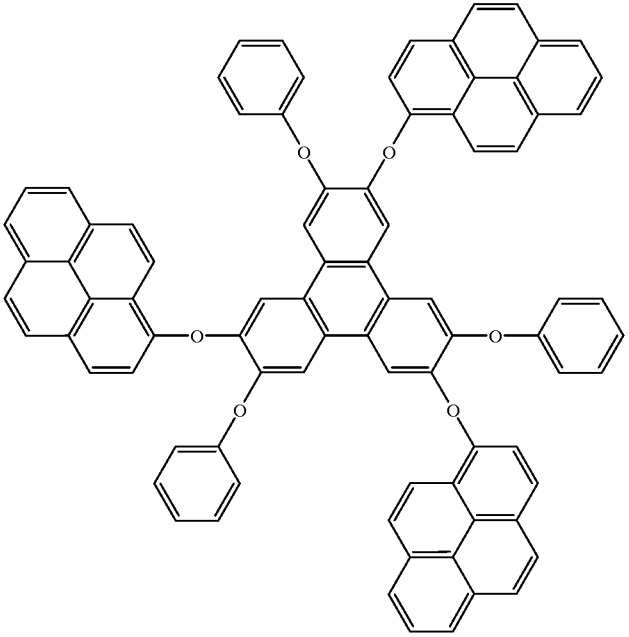 |

TABLE 1-continued
| No. | Chemical structure |
| --- | --- |
| 40 | 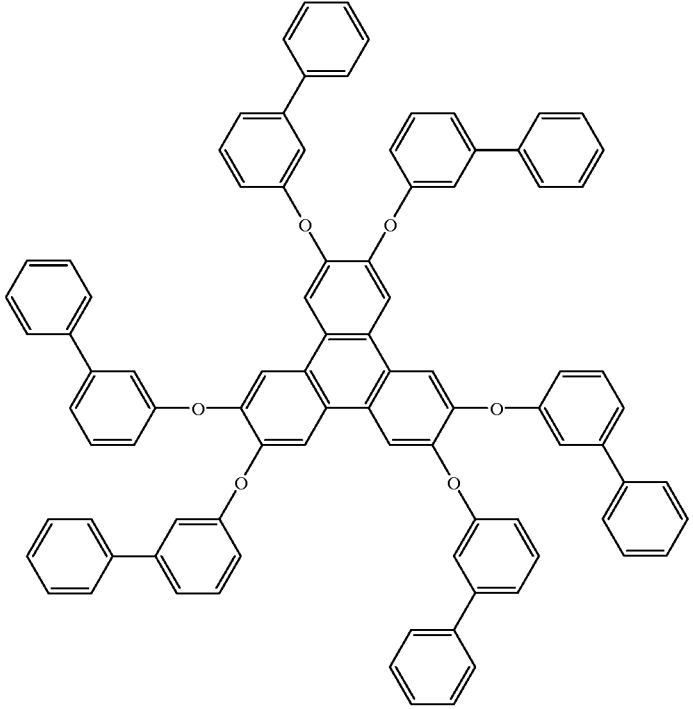 |
| 41 | 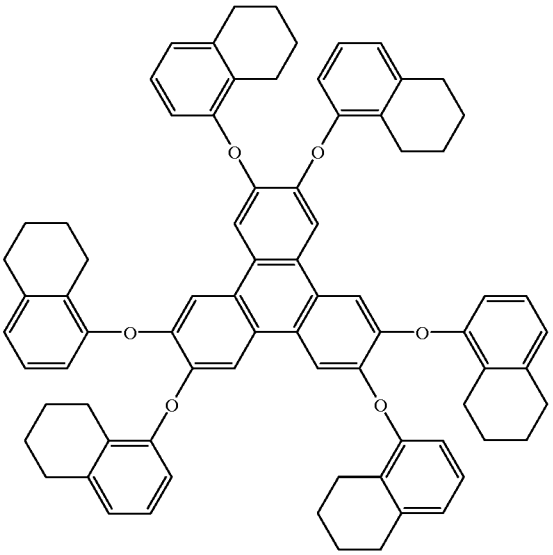 |

TABLE 1-continued
| No. | Chemical structure |
|---|---|
| 42 | 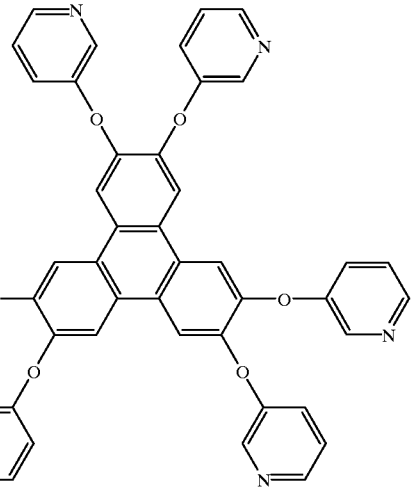 |
| 43 | 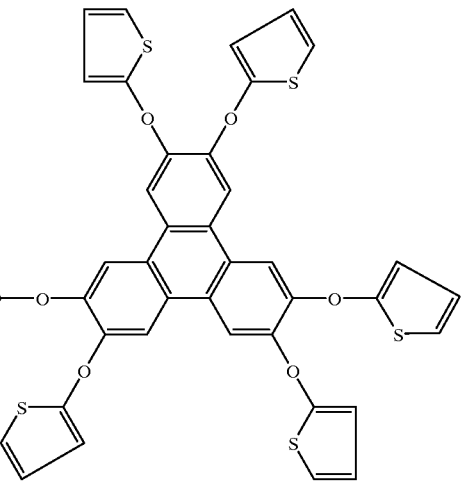 |
| 44 | 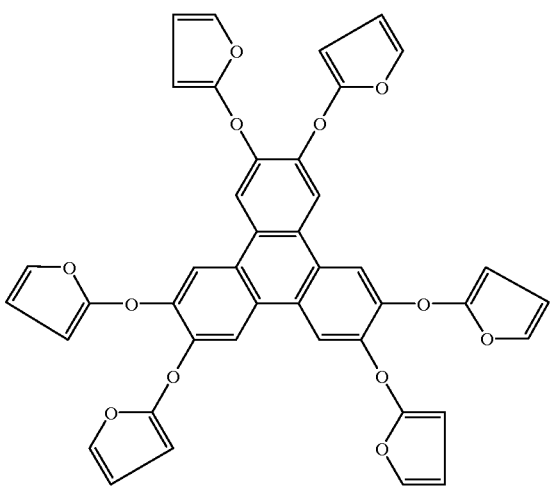 |

TABLE 1-continued
| No. | Chemical structure |
|---|---|
| 45 | 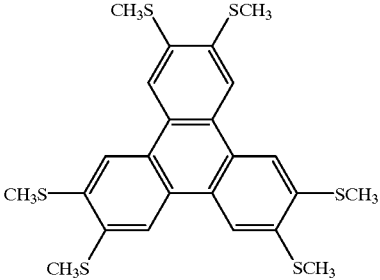 |
| 46 | 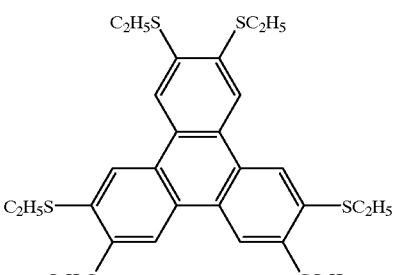 |
| 47 | 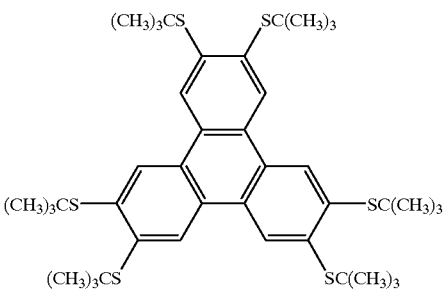 |
| 48 | 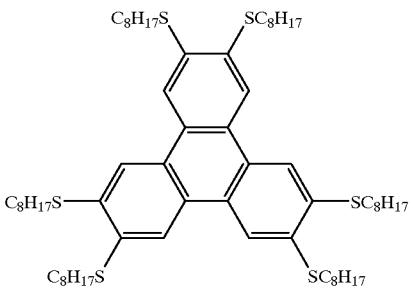 |
| 49 | 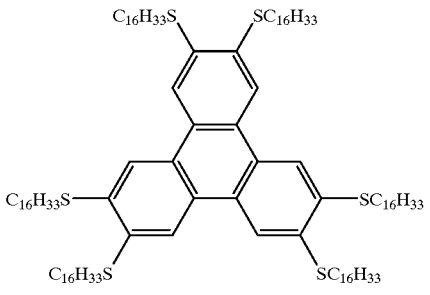 |

TABLE 1-continued

| No. | Chemical structure |
|---|---|
| 50 | Triphenylene with substituents: CH$_3$S, SC$_2$H$_5$, C$_2$H$_5$S, SCH$_3$, CH$_3$S, SC$_2$H$_5$ |
| 51 | Triphenylene with substituents: CH$_3$O, SC$_8$H$_{17}$, C$_8$H$_{17}$S, OCH$_3$, CH$_3$S, SC$_8$H$_{17}$ |
| 52 | Triphenylene with substituents: CH$_3$OCH$_2$S, SCH$_2$OCH$_3$, CH$_3$OCH$_2$S, SCH$_2$OCH$_3$, CH$_3$OCH$_2$S, SCH$_2$OCH$_3$ |
| 53 | Triphenylene with six benzyl-thio (PhCH$_2$S / SCH$_2$Ph) substituents |

TABLE 1-continued
| No. | Chemical structure |
|---|---|
| 54 | 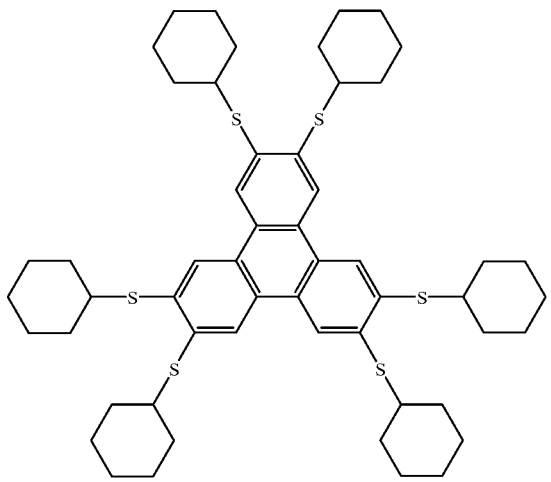 |
| 55 | 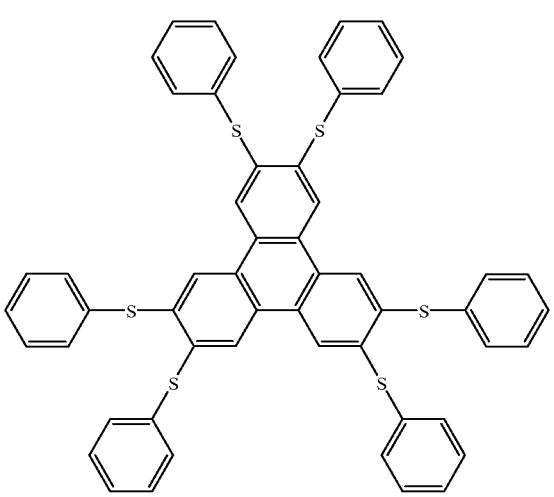 |
| 56 | 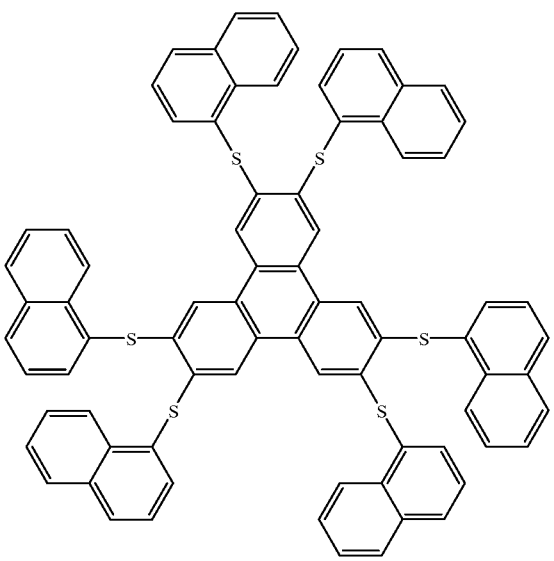 |

TABLE 1-continued
| No. | Chemical structure |
| --- | --- |
| 57 | 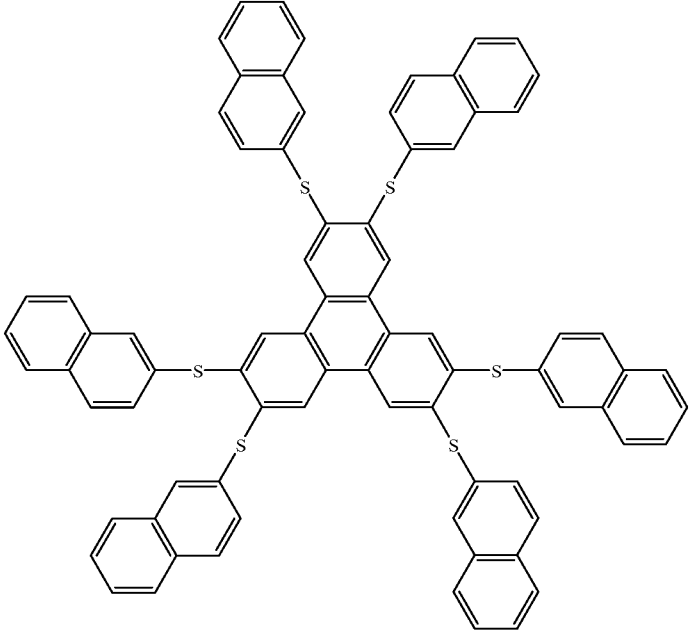 |
| 58 | 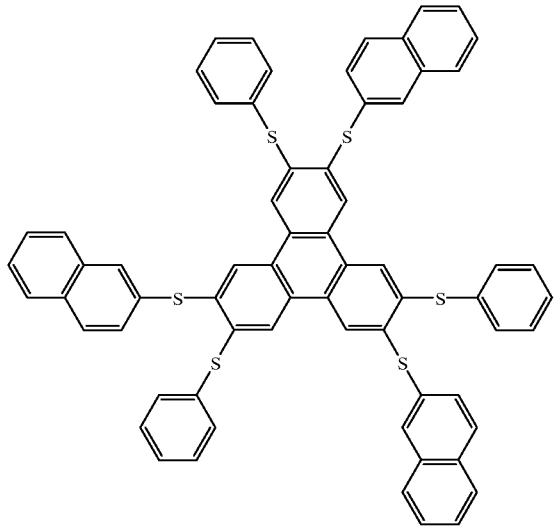 |

TABLE 1-continued
| No. | Chemical structure |
|---|---|
| 59 | 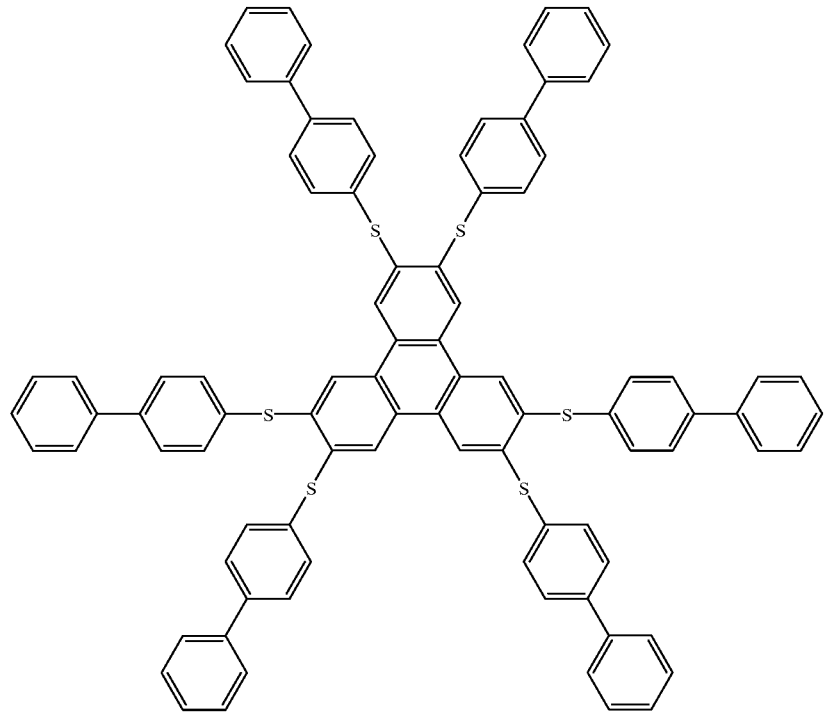 |
| 60 | 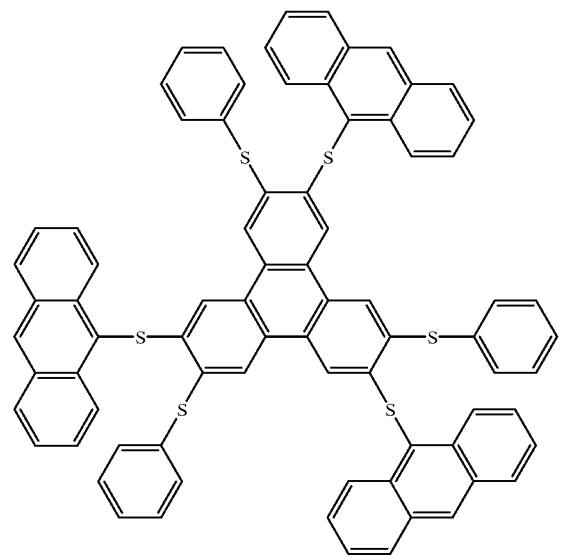 |

TABLE 1-continued

| No. | Chemical structure |
|---|---|
| 61 | 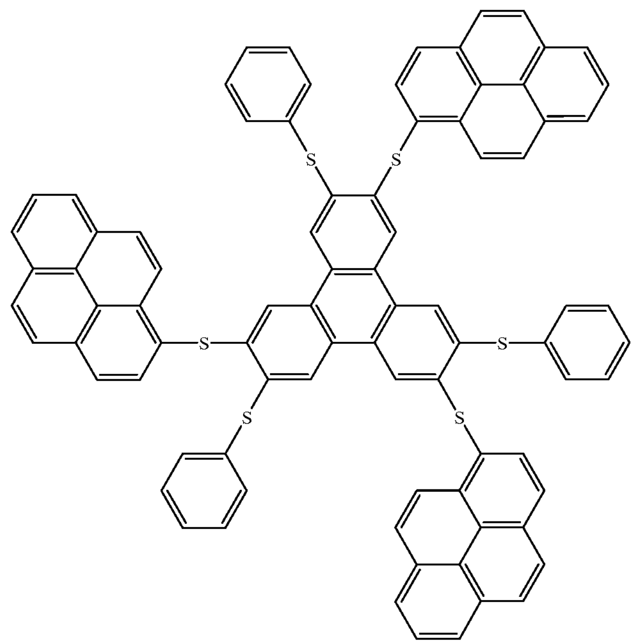 |
| 62 | 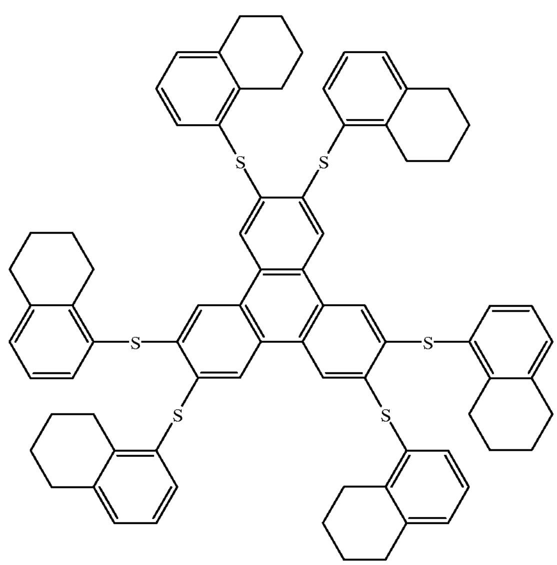 |

TABLE 1-continued
| No. | Chemical structure |
|---|---|
| 63 | 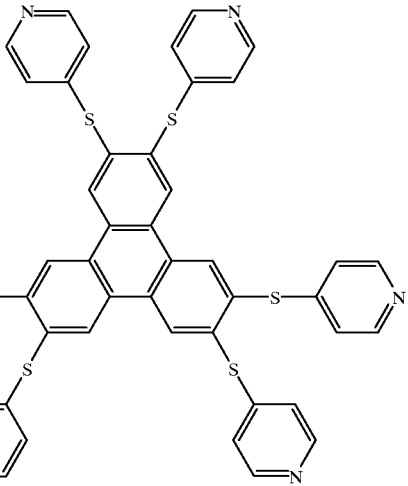 |
| 64 | 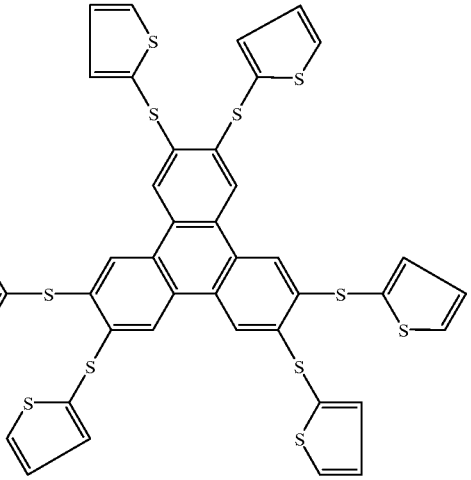 |
| 65 | 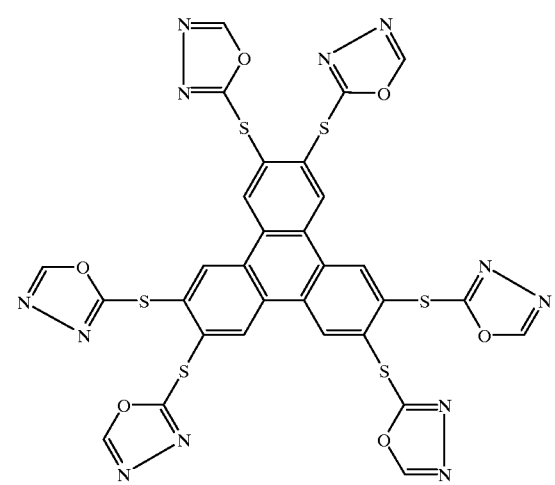 |

TABLE 1-continued

| No. | Chemical structure |
|---|---|
| 66 | 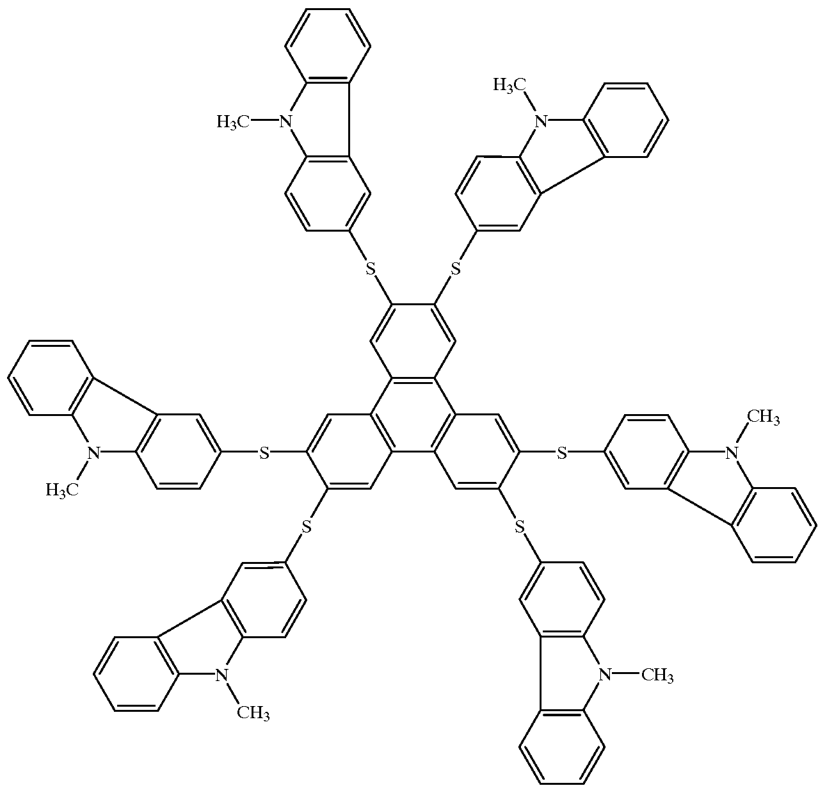 |
| 67 | 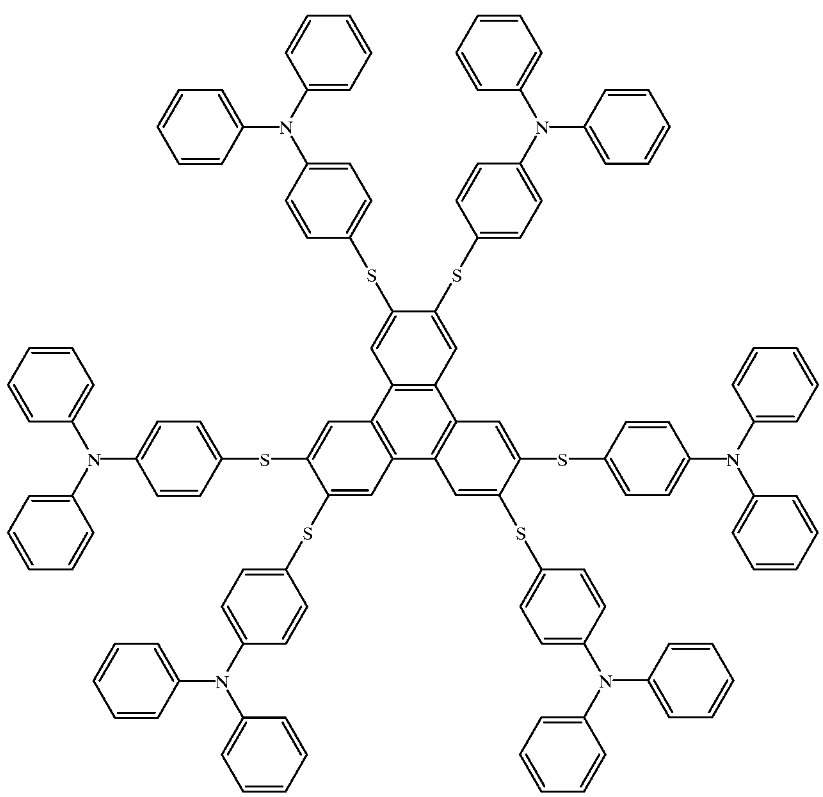 |

TABLE 1-continued
| No. | Chemical structure |
|---|---|
| 68 | 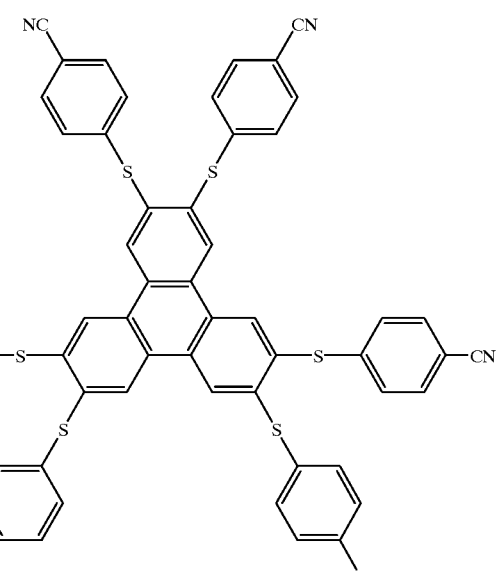 |
| 69 | 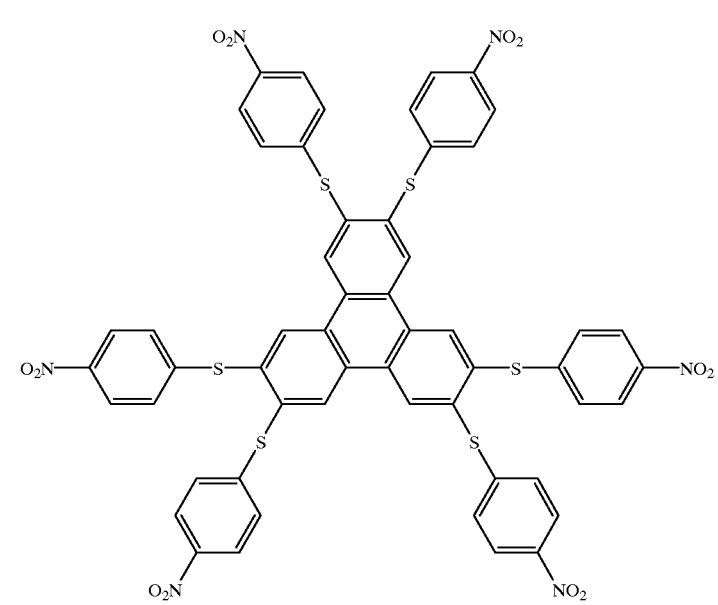 |

TABLE 1-continued

| No. | Chemical structure |
|---|---|
| 70 | *hexakis(4-trifluoromethoxyphenylthio)triphenylene* |
| 71 | *hexakis(dimethylamino)triphenylene* |
| 72 | *hexakis(di-n-butylamino)triphenylene* |

TABLE 1-continued
| No. | Chemical structure |
|---|---|
| 73 | 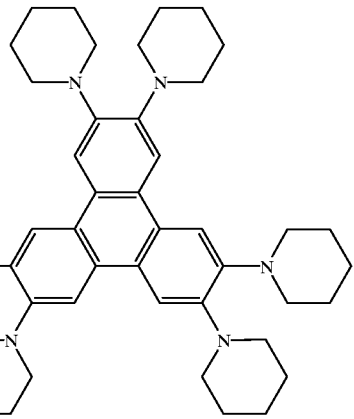 |
| 74 | 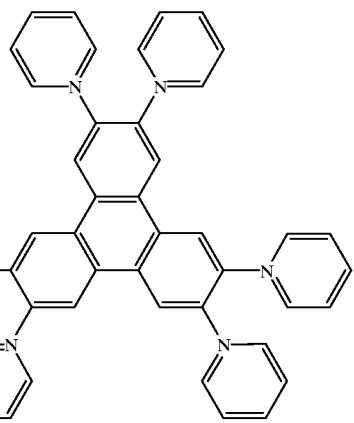 |
| 75 | 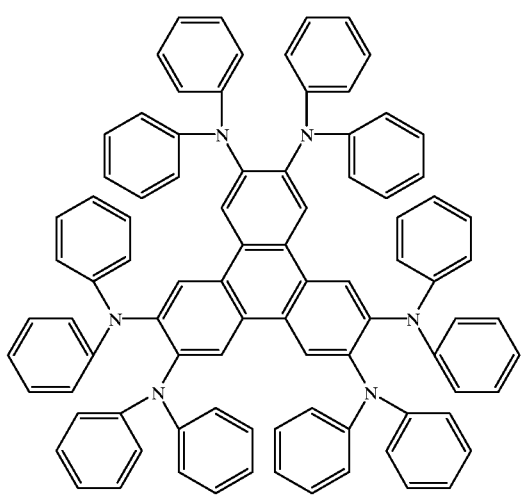 |

TABLE 1-continued

| No. | Chemical structure |
|---|---|
| 76 | 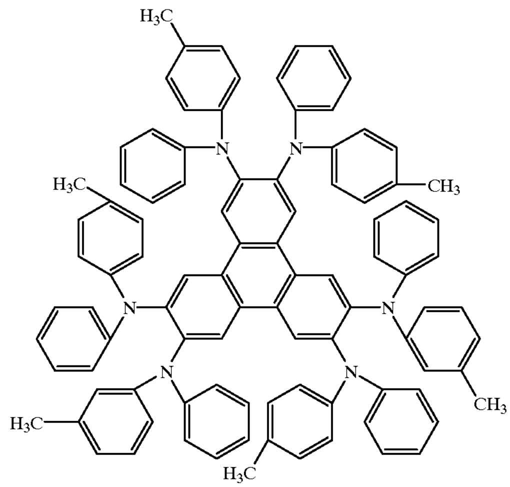 |
| 77 | 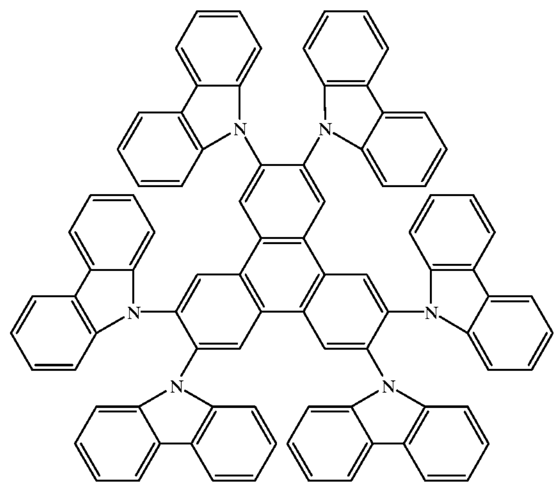 |

In the formula (II), $R^1$, $R^2$ and $R^4$ to $R^{11}$ have the same meanings as those of $R^1$ to $R^6$ in the formula (I), and $X^1$ to $X^{12}$ have the same meanings as those of $X^1$ to $X^6$ in the formula (I). And, at least one combination of adjacent $X^1$—$R^1$ and $X^2$—$R^2$, $X^5$—$R^5$ and $X^6$—$R^6$, $X^7$—$R^7$ and $X^8$—$R^8$, or $X^9$—$R^9$ and $X^{10}$—$R^{10}$ is a non-substituted mono-hetero-cyclic ring, a substituted mono-hetero-cyclic ring, a non-substituted fused poly-hetero-cyclic ring or a substituted fused poly-hetero-cyclic ring, and $A^1$ is a chemically rational organic residue which is composed of C, H and O, or is composed of C, H, O and S, and has a molecular weight of 500 or less.

Further, in the formula (III), $R^1$, $R^2$ and $R^4$ to $R^{17}$ have the same meanings as those of $R^1$ to $R^6$ in the formula (I), and $X^1$ to $X^{18}$ have the same meanings as those of $X^1$ to $X^6$ in the formula (I). And, at least one combination of adjacent $X^1$—$R^1$ and $X^2$—$R^2$, $X^5$—$R^5$ and $X^6$—$R^6$, $X^7$—$R^7$ and $X^8$—$R^8$, $X^9$—$R^9$ and $X^{10}$—$R^{10}$, $X^{13}$—$R^{13}$ and $X^{14}$—$R^{14}$, or $X^{15}$—$R^{15}$ and $X^{16}$—$R^{16}$ is a non-substituted mono-hetero-cyclic ring, a substituted mono-hetero-cyclic ring, a non-substituted fused poly-hetero-cyclic ring or a substituted fused poly-hetero-cyclic ring, and $A^2$ is a chemically rational organic residue which is composed of C, H and O, or is composed of C, H, O and S, and has a molecular weight of 500 or less.

In the formulae (II) and (III), each of $A^1$ and $A^2$ is preferably a substituted or non-substituted alkylene group, a substituted or non-substituted alicyclic group, a substituted or non-substituted aromatic ring group or a substituted or non-substituted hydrocarbon group.

Examples of the substituted or non-substituted alkylene group include methylene, ethylene, propylene, butylene, sec-butylene, tert-butylene, pentylene, hexylene, heptylene, octylene, stearylene, trichloromethylene and trifluoromethylene.

Examples of the alicyclic group include cyclopropylene, cyclohexylene, 1,3-cyclohexadienylene, 2-cyclopenten-1-ylene, 2,4-cyclopentadien-1-ylidenylene, benzylene and 2,2-dimethylbenzylene.

Examples of the substituted or non-substituted aromatic ring group include phenylene, tolylene, naphthylene, anthranylene, phenanthrenylene, fluorenylene, acenaphthylene, azulenylene, heptalenylene, acenaphthylenylene, pyrenylene, biphenylene, 4-ethylbiphenylene, terphenylene, quaterphenylene, benz[a]anthranylene, triphenylenylen, 2,3-benzofluorenylene and 3,4-benzopyrenylene.

Further, each of $A^1$ and $A^2$ may be a group formed by combining groups of different kinds such as a combination of an alkylene group and an aromatic ring group, a combination of an alkylene group and an alicyclic group, or the like, and the groups of a combination may be combined through an oxygen atom, a sulfur atom or a nitrogen atom.

In the formulae (II) and (III), the substituted or non-substituted alkylene group, the substituted or non-substituted alicyclic group and the substituted or non-substituted aromatic ring group in the definition of $A^1$ and $A^2$ may contain a substituent included in the groups defined as $R^1$ to $R^{11}$ or $R^1$ to $R^{17}$.

Table 2 shows specific examples of the compounds of the formulae (II) and (III), while the compounds of the formulae (II) and (III) shall not be limited thereto.

TABLE 2

| No. | Chemical structure |
| --- | --- |
| 78 | 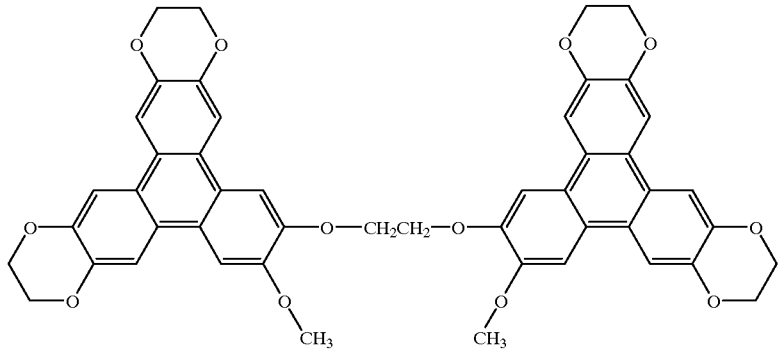 |
| 79 | 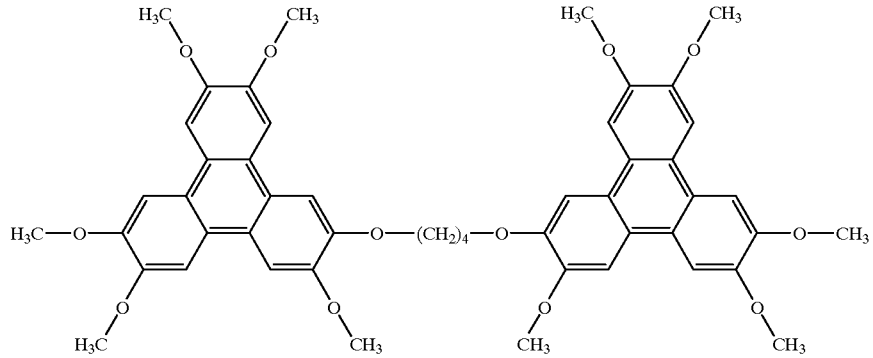 |
| 80 | 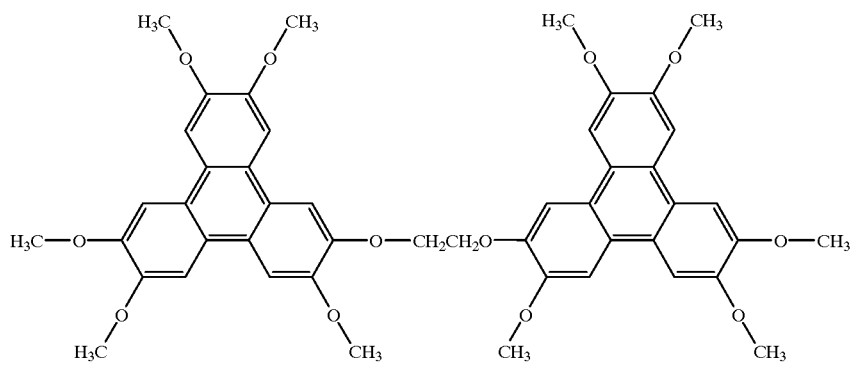 |

TABLE 2-continued
| No. | Chemical structure |
|---|---|
| 81 | 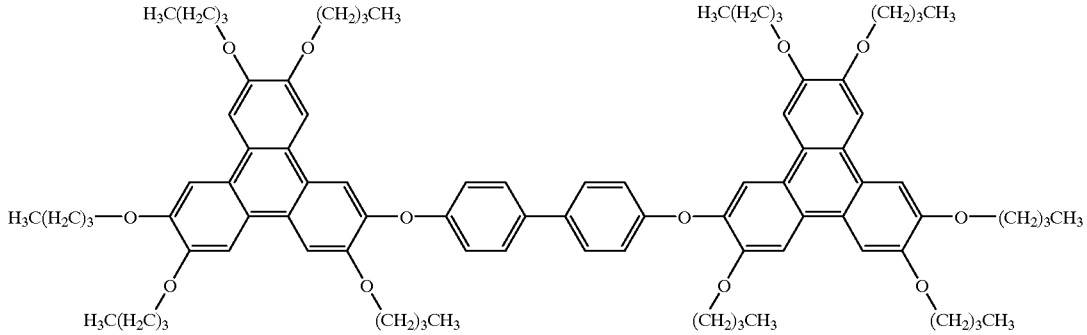 |
| 82 | 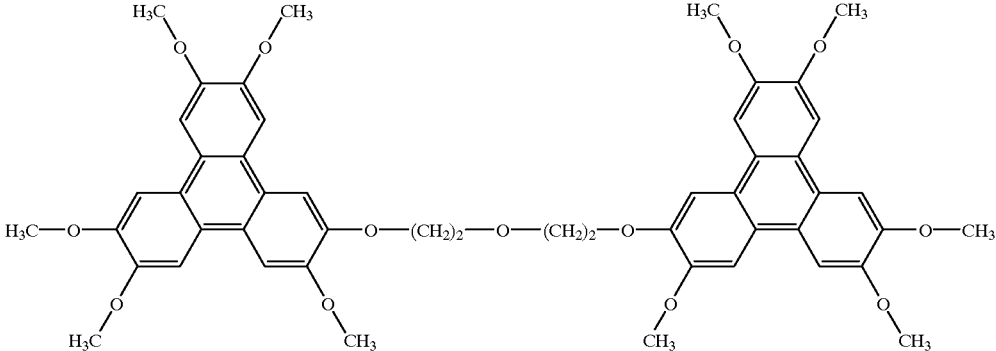 |
| 83 | 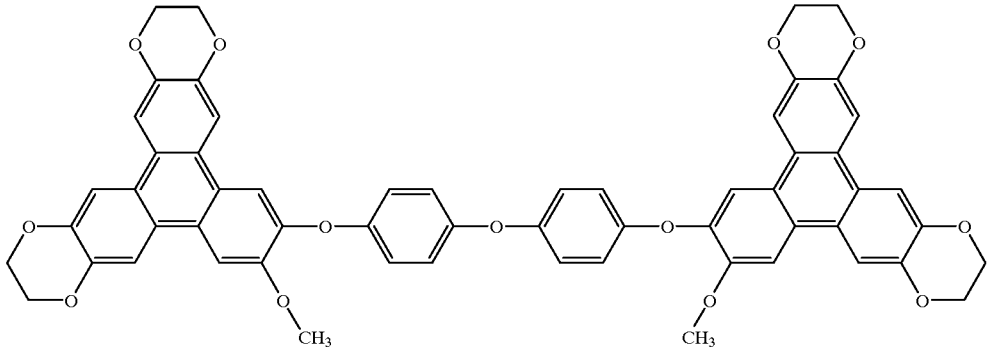 |
| 84 | 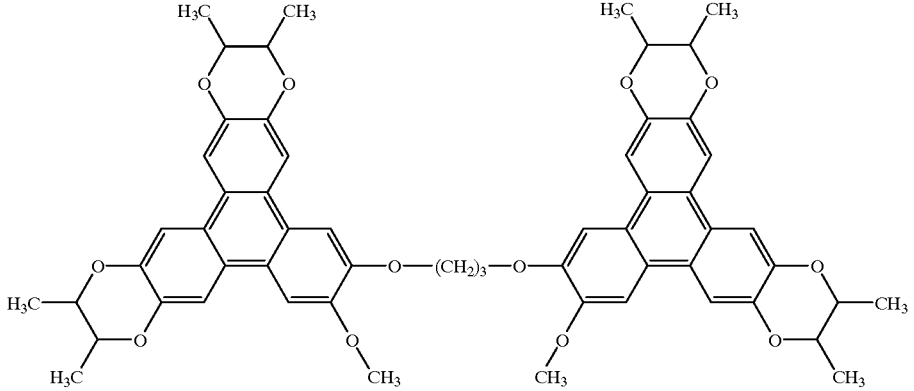 |

TABLE 2-continued
| No. | Chemical structure |
|---|---|
| 85 | 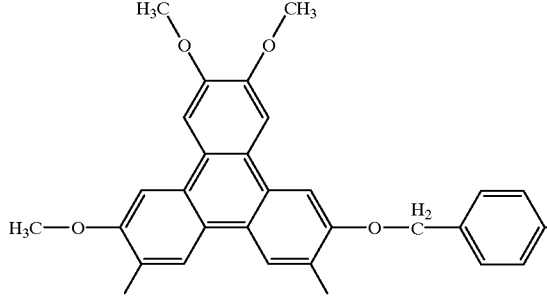 |
| 86 | 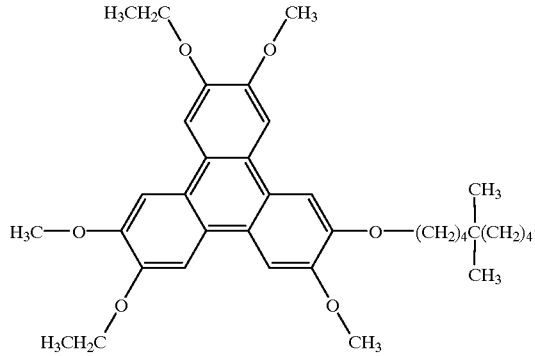 |
| 87 | 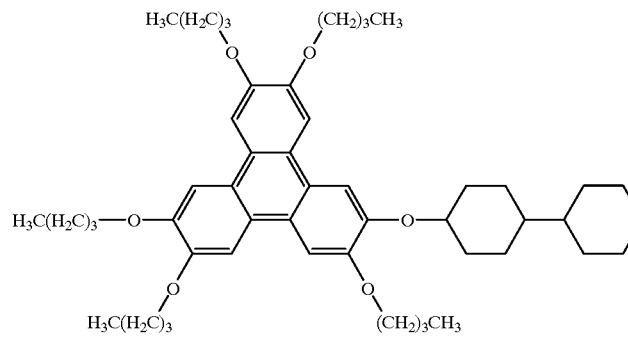 |
| 88 | 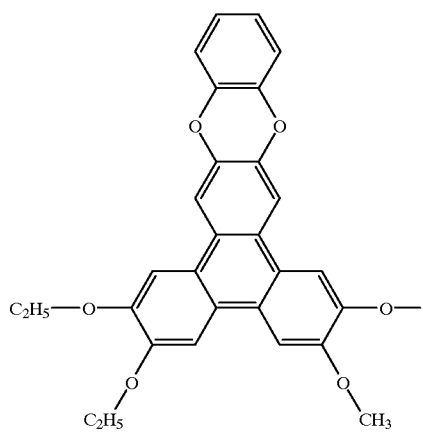 |

TABLE 2-continued
| No. | Chemical structure |
|---|---|
| 89 | 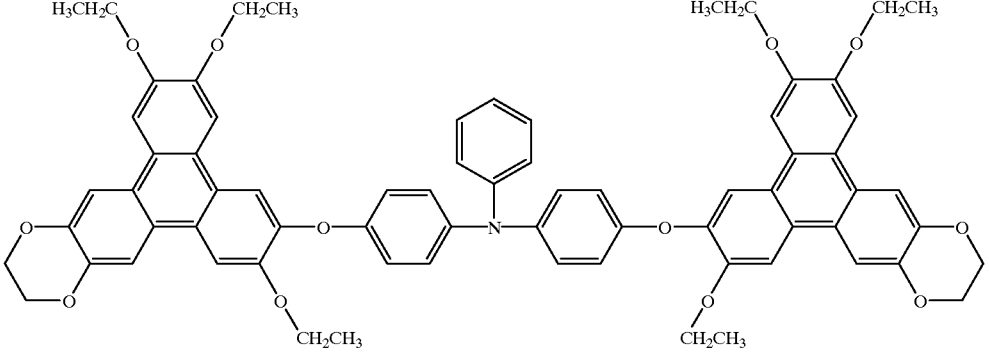 |
| 90 | 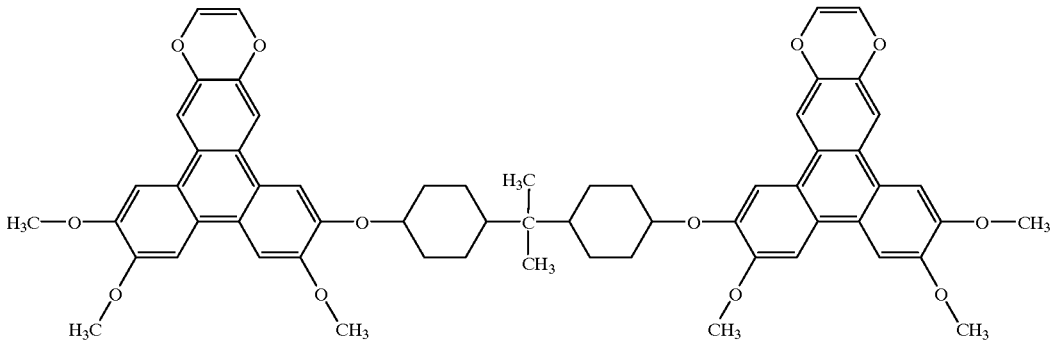 |
| 91 | 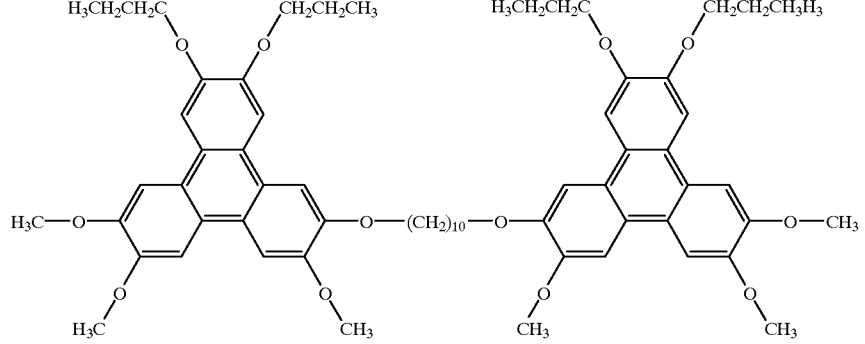 |

TABLE 2-continued
| No. | Chemical structure |
|---|---|
| 92 | 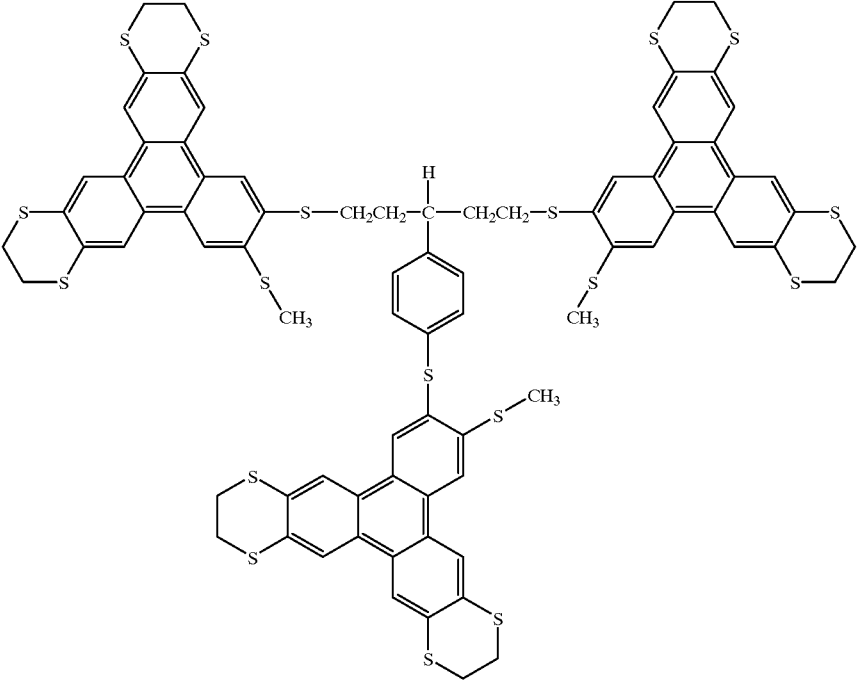 |
| 93 | 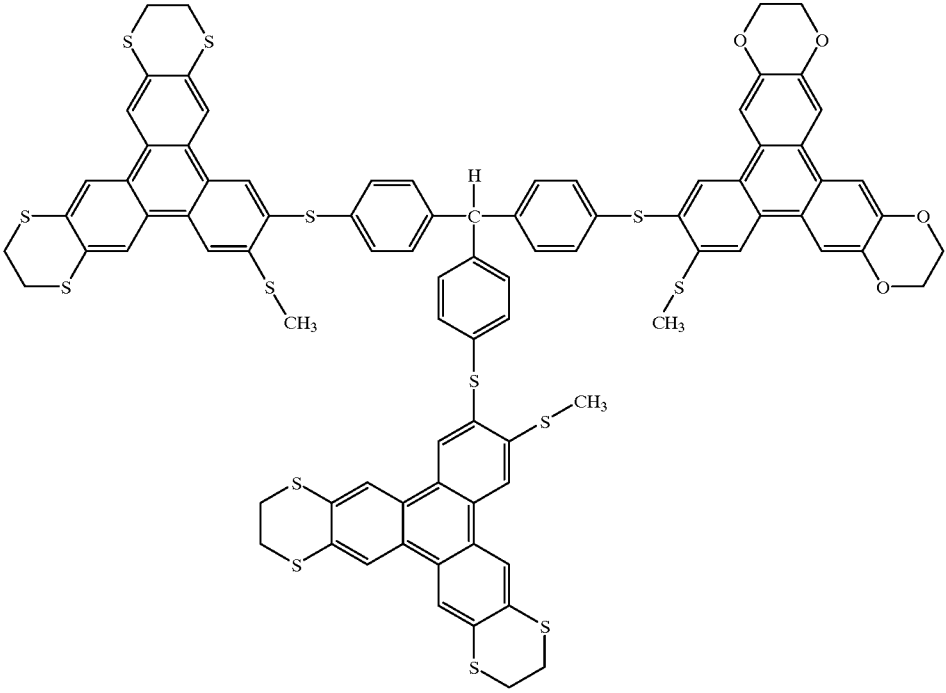 |

TABLE 2-continued

| No. | Chemical structure |
| --- | --- |
| 94 | 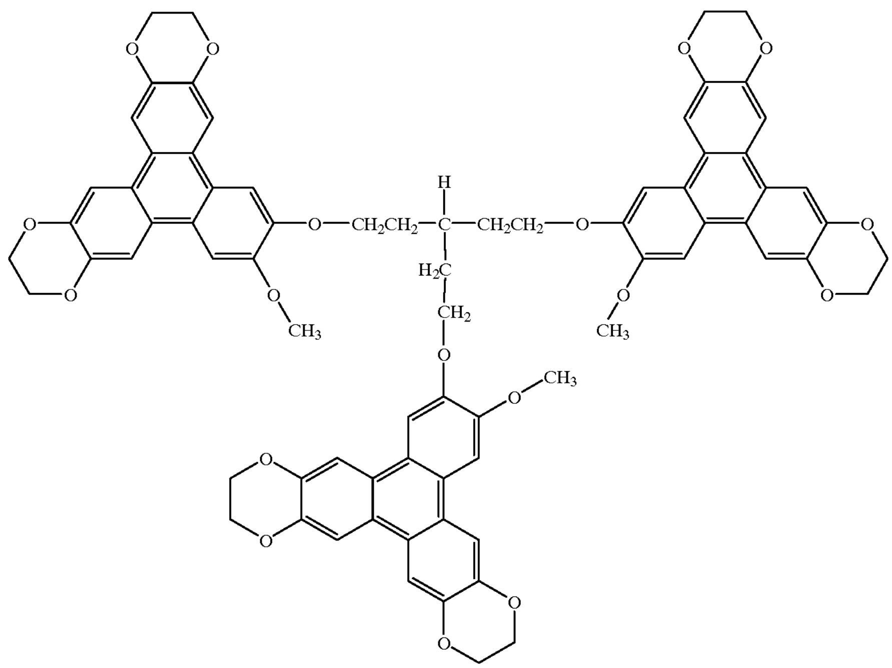 |
| 95 | 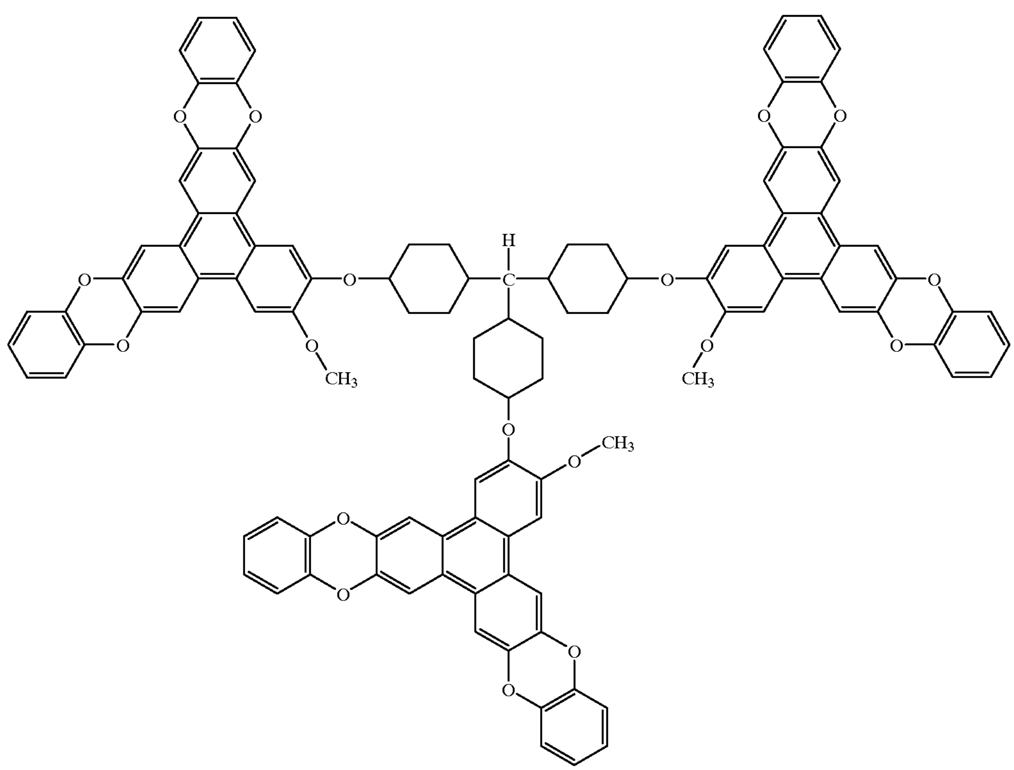 |

TABLE 2-continued
| No. | Chemical structure |
| --- | --- |
| 96 | 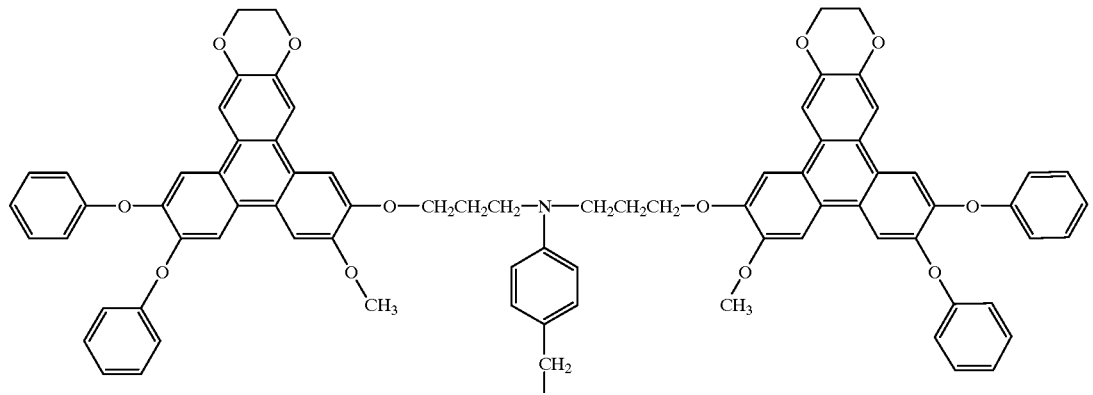 |
| 97 | 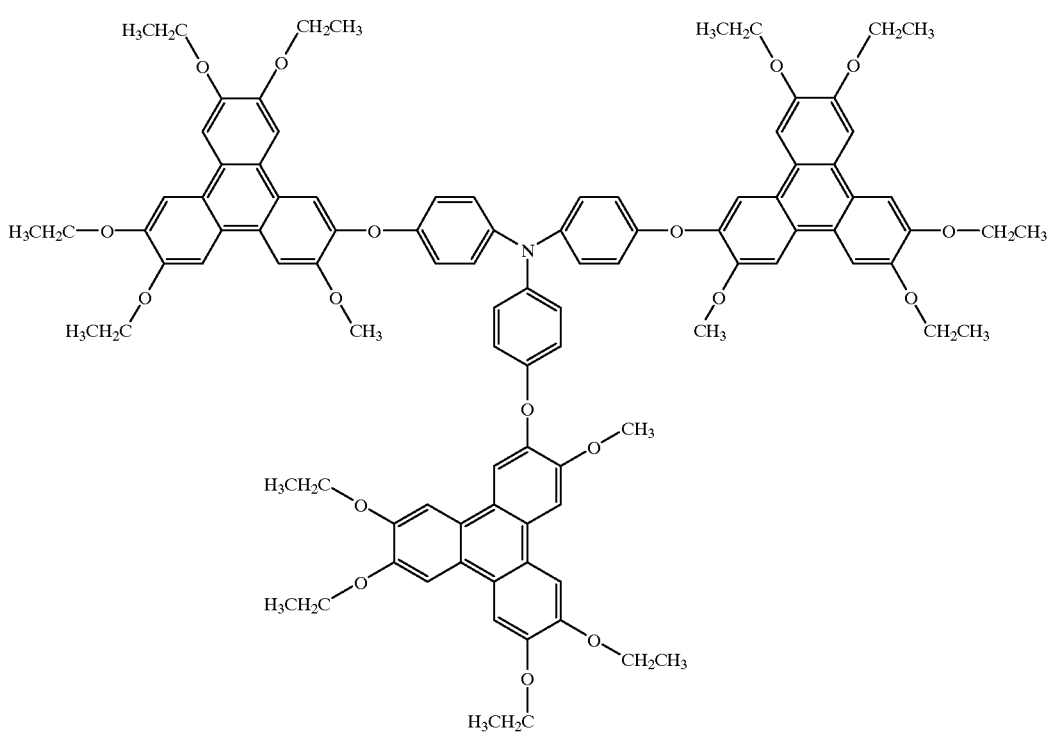 |

TABLE 2-continued

| No. | Chemical structure |
|---|---|
| 98 | 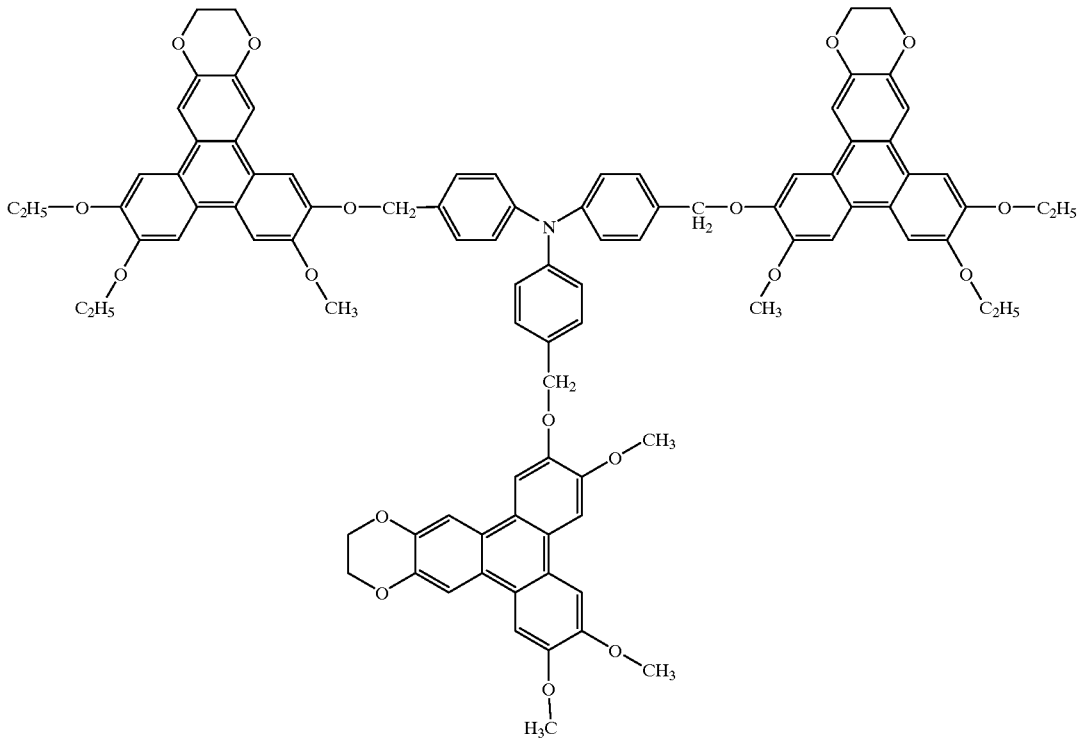 |

The material of the present invention may be used together with other hole-injecting material or electron-injecting material in one layer.

The organic EL device has a structure in which a mono- or multi-layered organic thin film including a light-emitting layer is formed between an anode and a cathode. In a mono-layered device, a light-emitting layer is formed between the anode and the cathode. The light-emitting layer contains a light-emitting material, and in addition thereto, it may contain a hole-transporting material for transporting holes injected from the anode to the light-emitting material, or an electron-transporting material for transporting electrons injected from the cathode to the light-emitting material. Some light-emitting materials contain the capability of injecting holes or electrons. The multi-layered organic EL device has one of laminated-layer structures, for example, of (anode/hole-injecting zone/light-emitting layer/cathode), (anode/light-emitting layer/electron-injecting zone/cathode) and (anode/hole-injecting zone/light-emitting layer/electron-injecting zone/cathode). The compound of the formula [1] can be used in any one of the above device structures. The material of the formula (I) (including the materials of the formulae (II) and (III)) has the function of injecting holes from a cathode to a hole-injecting zone and the function of transporting and injecting the injected holes into a light-emitting layer. When the hole-injecting zone is formed of two or more layers, therefore, the material of the formula (I) (including the materials of the formulae (II) and (III)) can be used in any one these hole-injecting layers. Further, since they have fluorescence, they can be used as a light-emitting layer. Further, they can be used as an electron-transporting material by adding an electron-attracting substituent. The material of the present invention gives an amorphous thin film, and is therefore advantageous in storage as a thin film for a long period of time and a light emission life when the device is activated. Further, since the material of the present invention has a low ionization potential as a film and shows excellent adhesion to an electrode made of a metal such as ITO, it can be suitably used in a hole-injecting layer to be in contact with an ITO electrode (anode). Further, in view of the smoothness of a film formed of the material of the present invention and the capability of injecting holes into a light-emitting material, the material of the present invention can be also suitably used in a hole-injecting layer to be in contact with a light-emitting material.

In addition to the material of the present invention, the light-emitting layer may contain a known light-emitting material, a known dopant, a known hole-transporting material or a known electron-transporting material as required. When the organic EL device has a two-layered structure, the light-emitting layer and the hole-injecting layer are separated. Owing to this structure, the efficiency in injecting holes from the hole-injecting layer to the light-emitting layer improves, and the device is improved in light emission brightness and light emission efficiency. In this case, preferably, for light emission, the light-emitting material itself, used in the light-emitting layer, has the capability of injecting electrons, or the light-emitting layer contains an electron-transporting material. There is another two-layered structure formed of a light-emitting layer and an electron-injecting layer. In this case, preferably, the light-emitting material itself has the capability of injecting holes, or the light-emitting layer contains a hole-transporting material.

In a three-layered structure, the device has a light-emitting layer, a hole-injecting layer and an electron-injecting layer, so that the efficiency in the recombination of holes and electrons in the light-emitting layer is improved. When the organic EL device is formed so as to have a multi-layered structure as described above, the decrease in brightness and life caused by quenching can be prevented. In the device having the above multi-layered structure, a light-emitting material, a dopant, a hole-transporting material for transporting a carrier and an electron-transporting material may be used in combination as required. Further, the use of a dopant improves the light emission brightness and the light emission efficiency, and gives red or blue light. Further, each of the hole-injecting zone, the light-emitting layer and the electron-injecting zone may be formed of at least two layers. These layers may be formed by a selection depending upon various factors such as energy level, heat resistance and adhesion to an organic layer or a metal electrode.

Although not specially limited, examples of the light-emitting material or the dopant which are usable in combination with, or independently of, the material of the present invention include anthracene, naphthalene, phenanthrene, pyrene, tetracene, coronene, chrysene, fluorescein, perylene, phthaloperylene, naphthaloperylene, perinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, triphenylamine, benzidine type triphenylamine, styrylamine type triphenylamine, diamine type triphenylamin, pyran, thiopyran, polymethine, merocyanine, an imidazole-chelated oxynoid compound, porphyrin metal complex, phthalocyanine complex, rare earth metal complex, quinacridone, rubrene and fluorescent dyestuffs for dyestuff laser or for brightness. When the above compound, which is generally called an organic fluorescence dyestuff, is added to the material of the present invention, excited energy generated by the recombination of holes and electrons in the light-emitting layer moves efficiently to the organic fluorescence dyestuff, whereby high-intensity light color inherent to the fluorescence dyestuff can be obtained.

Specific examples of the material effective as a light-emitting material or dopant include metal complex compounds such as aluminum tris(8-hydroxyquinolinate), aluminum tris(2-methyl-8-hydroxyquinolinate), gallium tris(8-hydroxyquinolinate), beryllium bis(10-hydroxybenzo[h] quinolinate), zinc bis(10-hydroxybenzo[h]quinolinate), chlorogallium bis(2-methyl-8-quinolinate), gallium bis(2-methyl-8-quinolinate) (o-cresolate), aluminum bis(2-methyl-8-quinolinate) (1-naphtholate), gallium bis(2-methyl-8-quinolinate) (2-naphtholate), gallium bis(2-methyl-8-quinolinate)phenolate, zinc bis(o-(2-benzooxazolyl)phenolate), zinc bis(o-(2-benzothiazolyl) phenolate) and zinc bis(o-(2-benzotriazolyl)phenolate), aromatic amine-containing compounds such as N,N,N',N'-(4-($\alpha,\alpha$'-dimethylbenzyl)phenyl)-anthranyl-9,10-diamine and 9,10-bis(4-(di-p-tolylamino)phenyl)anthracene, bisstylyl-containing compounds such as 4,4'-bis($\beta,\beta$-diphenylvinyl) biphenyl, 4,4-bis($\beta$-(N-ethyl-3-carbozolyl)vinyl)biphenyl and 4,4'-bis(p-diphenylaminostyryl)biphenyl, perylene, perylene tetracarboxylic acid diimide derivatives, 3-(2'-benzothiazolyl)-7-diethylaminocoumarin (coumarin 6), 4-(dicyanomethylene)-2-methyl-6-(p-dimethylaminostyryl)-4-H-pyran (DCM), Nile Red, diphenylanthracene and its derivatives, quinacridone and its derivatives, and rubrene and its derivatives. However, the above light-emitting material shall not be limited to the above materials.

The hole-transporting material includes compounds which have the capability of transporting holes, exhibit an effect on the injection of holes from an anode and an excellent effect on the injection of holes to a light-emitting layer or a light-emitting material, prevent the migration of excitons generated in a light-emitting layer into an electron-injecting zone or an electron-transporting material and have the excellent capability of forming a thin film. Specific examples of the hole-transporting material which can be used together with, or independently of, the material of the present invention include a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electrically conductive polymer. However, the hole-transporting material shall not be limited to the above materials.

The hole-transporting material that can be effectively used in the organic EL device of the present invention includes an aromatic tertiary amine derivative or a phthalocyanine derivative other than the material of the present invention. Although not specially limited, specific examples of the tertiary amine derivative include triphenylamine, tritolylamine, tolyldiphenylamine, N,N'-diphenyl-N,N'-di (3-methylphenyl)-1,1-biphenyl-4,4'-diamine, N,N,N',N'-tetra(4-methylphenyl)-1,1'-phenyl-4,4'-diamine, N,N,N',N'-tetra(4-methylphenyl)-1,1'-biphenyl-4,4'-diamine, N,N'-diphenyl-N,N'-di(1-naphthyl)-1,1'-biphenyl-4,4'-diamine, N,N'-di(methylphenyl)-N,N'-di(4-n-butylphenyl) phenanthrene-9,10-diamine, 4,4',4"-tris(N-(3-methylphenyl)-N-phenylamino)triphenylamine, 1,1-bis(4-di-p-tolyaminophenyl)cyclohexane, and origomers or polymers having aromatic tertiary amine structures of these.

Specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc. However, the phthalocyanine derivative shall not be limited to the above compounds.

The electron-transporting material includes materials which are capable of transporting electrons, exhibit an effect on the injection of electrons from a cathode and an excellent effect on the injection of electrons into a light-emitting layer or light-emitting material, prevent the migration of excitons generated in the light-emitting layer into the hole-injecting zone and have the excellent capability of forming a thin film. Examples of the electron-transporting material include fluorenone, anthraquinodimethane, diphenoquinone, thiopyran dioxide, oxazole, oxadiazole, triazole, imidazole, perylenetetracarboxylic acid, fluorenylidenemethane, anthraquinodimethane, anthrone, and derivatives of these. However, the electron-transporting material shall not be limited to these.

The hole-transporting material may be sensitivity-increased by incorporating an acceptor material, and the electron-injecting material may be sensitivity-increased by incorporating a donor material.

In the organic EL device of the present invention, the electron-transporting material which is more effective is a metal complex compound or a nitrogen-containing five-membered derivative. Specific examples of the metal complex compound include lithium 8-hydroxyquinolinate, zinc bis(8-hydroxyguinolinate), copper bis(8-hydroxyguinolinate), manganese bis(8-hydroxyquinolinate), aluminum tris(8-hydroxyquinolinate), aluminum tris(2-methyl-8-hydroxyquinolinate), gallium tris (8-hydroxyquinolinate), beryllium bis(10-hydroxybenzo[h] quinolinate), zinc bis(10-hydroxybenzo[h]quinolinate), chlorogallium bis( 2-methyl-8-quinolinate), gallium bis(2-methyl-8-guinolinate)(o-cresolate), aluminum bis(2-methyl-8-quinolinate)(1-naphtholate), gallium bis(2-methyl-8-quinolinate)(2-nal)htholate), gallium bis(2-methyl-8-quinolinate)phenolate, zinc bis(o-(2-benzooxazolyl) phenolate), zinc bis(o-(2-benzothiazolyl)phenolate) and zinc bis(o-(2-benzotriazolyl)phenolate). However, the metal complex compound shall not be limited to these. The nitrogen-containing five-membered derivative is preferably oxazole, thiazole, thiadiazole ,a triazole and derivatives thereof. Specific examples of the above nitrogen-containing five-membered derivative include 2,5-bis(1-phenyl)-1,3,4-oxazole, 1,4-bis(2-(4-methyl-5-phenyloxazolyl)benzene, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)] benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the nitrogen-containing five-membered derivative shall not be limited to these.

Each of the light-emitting layer, the hole-injecting layer and the electron-injecting layer in the present invention may be formed of two or more compounds. Specific effects of the present constitution are that light is effectively emitted by adding an organic fluorescence dyestuff to the light-emitting layer, that sensitivity is increased by adding an acceptor material to the hole-injecting material or by adding an donor material to the electron-injecting material and that an amorphous film is formed by incorporating the material of the present invention.

As an electrically conductive material for the anode of the organic EL device, it is preferred to use a material having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electrically conductive resins such as polythiophene and polypyrrole.

As an electrically conductive material for the cathode, it is preferred to use a material having a work function of smaller than 4 eV. The electrically conductive material includes magnesium, calcium, tin, lead, titanium, yttrium, lithium, ruthenium, manganese, and alloys of these. However, the electrically conductive material shall not be limited to these. Typical examples of the alloys include magnesium/silver, magnesium/indium and lithium/aluminum, while the alloys shall not be limited to these. The ratio of the alloys is controlled on the basis of the temperature of a vapor deposition source, atmosphere and a vacuum degree, and a proper ratio is selected. Each of the anode and the cathode may be formed of two layers or more as required.

For the effective light emission of the organic EL device, at least one of the electrodes is desirably transparent in the light emission wavelength region of the device. Further, the substrate is desirably transparent. The transparent electrode is produced from the above electrically conductive material by a deposition method or a sputtering method such that a predetermined transparency is secured. The electrode which forms a light emission surface preferably has a light transmittance of at least 10%. The substrate is not specially limited so long as it has mechanical and thermal strength and is transparent. For example, it is selected from glass substrates and substrates of transparent resins such as a polyethylene substrate, a polyethylene terephthalate substrate, a polyether sulfone substrate and a polypropylene substrate. The substrate may have any form such as the form of a plate or a film.

Each of the layers forming the organic EL device of the present invention can be formed by any one of dry film forming methods such as a vacuum deposition method and a sputtering method and wet film forming methods such as a spin coating method and a dipping method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain even when an electric field is applied. Generally, the thickness of each layer is preferably in the range of from 5 nm to 10 $\mu$m, more preferably 10 nm to 0.2 $\mu$m.

In the wet film forming method, a material for forming an intended layer is dissolved or dispersed in a proper solvent such as chloroform, tetrahydrofuran or dioxane, and a thin film is formed from the solution or dispersion. The solvent shall not be limited to these. For improving the film formability and preventing the occurrence of pinholes, the above solution or dispersion for forming the layer may contain a proper resin and a proper additive.

The resin for use in the present invention includes insulating resins such as polystyrene, polycarbonate, polyarylate, polyester, polyamide, polyurethane, polysulfone, polymethyl methacrylate, polymethyl acrylate and cellulose, photo-conductive resins such as poly-N-vinylcarbazole and polysilane, and electrically conductive resins such as polythiophene and polypyrrole. The above additive includes an antioxidant, an ultraviolet absorbent and a plasticizer.

The organic EL device of the present invention may be improved in stability against temperature, humidity and atmosphere by forming a protective layer on its surface, or by protecting the entire device with a silicon oil or a resin.

In the present invention, the light emission efficiency and the light emission brightness can be improved by the use of the material of the present invention. Further, the organic EL device of the present invention is stable against heat and electric current and gives a practically acceptable light emission brightness at a low driving voltage, so that it excellently overcomes a conventional serious problem, a decrease in brightness in the continuous operation of light emission.

The organic EL device of the present invention can be applied to flat panel displays such as an on-wall television set, a flat light-emitting device, a light source for a copying machine or a printer, a light source for a liquid crystal display or a counter, a display signboard and a signal light, and it therefore has high industrial values. Further, the material of the present invention can be used not only in the field of an organic EL device, but also in the fields of an electrophotographic photoreceptor, a photoelectric converter, a solar cell, an image sensor, and the like.

EXAMPLES

The present invention will be explained more in detail with reference to Examples hereinafter.

According to DSC analysis, most of the materials which are provided by the present invention have a glass transition temperature of at least 100° C., a melting point of at least 250° C. and a decomposition temperature of at least 300° C. As compared with 4,4',4"-tris [N-(3-methylphenyl)-N-phenylamino]triphenylamine which is conventionally used as a noncrystalline hole-injecting material, the material of the present invention has a high glass transition temperature, a high melting point and a high decomposition temperature, and it is therefore seen that the material of the present invention has high heat resistance as a hole-injecting material for an organic EL device. Further, since the material of the present invention has low crystallizability or is free of crystallizability, it exhibits excellent adhesion to an anode substrate and a layer of an organic thin film, and it is excellently advantageous in durability of an organic thin film to environments, the light emission life of an organic EL device which is driven and the storage properties of an organic EL device.

Example 1

Compound (1) was vacuum-deposited on a cleaned glass substrate with ITO electrode, to obtain a hole-injecting layer having a thickness of 30 nm. Then, an aluminum tris(8-hydroxyquinolinate) complex was vacuum-deposited to form a light-emitting layer having a thickness of 50 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 120 (cd/m$^2$) at a direct current voltage of 5 V, a maximum light emission brightness of 19,000 (cd/m$^2$) and a light emission efficiency of 2.1 (lm/W).

Example 2

An organic EL device was prepared in the same manner as in Example 1 except that a hole-injecting layer was formed from a solution of Compound (2) in chloroform by a spin coating method. The device had the following light emission characteristics, i.e., a light emission brightness of 200 (cd/m$^2$) at a direct current voltage of 5 V, a maximum light emission brightness of 16,000 (cd/m$^2$) and a light emission efficiency of 2.0 (lm/W).

Example 3

Compound (4) was vacuum-deposited on a cleaned glass substrate with ITO electrode, to obtain a hole-injecting layer having a thickness of 40 nm. Then, N,N'-diphenyl-N,N'-(3-methylphenyl)-1,1'-biphenyl-4,4'-diamine was vacuum-deposited to obtain a second hole-injecting layer having a thickness of 10 nm. Further, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of $10^{-6}$ Torr at a substrate temperature of room temperature. The device had the following light emission characteristics, i.e., a light emission brightness of 240 (cd/m$^2$) at a direct current voltage of 5 V, a maximum light emission brightness of 27,000 (cd/m$^2$) and a light emission efficiency of 2.4 (lm/W).

Example 4

4,4',4"-tris[N-(3-methylphenyl)-N-phenylamino] triphenylamine was vacuum-deposited on a cleaned glass substrate with ITO electrode, to obtain a hole-injecting layer having a thickness of 40 nm. Then, Compound (3) was vacuum-deposited to obtain a second hole-injecting layer having a thickness of 10 nm. Further, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of $10^{-6}$ Torr at a substrate temperature of room temperature. The device had the following light emission characteristics, i.e., a light emission brightness of 260 (cd/m$^2$) at a direct current voltage of 5 V, a maximum light emission brightness of 36,000 (cd/m$^2$) and a light emission efficiency of 2.8 (lm/W).

Example 5

An organic EL device was prepared in the same manner as in Example 4 except that the 4,4',4"-tris[N-(3-methylphenyl)-N-phenylamino]triphenylamine for forming a first hole-injecting layer was replaced with 4,4',4"-tris[N-(1-naphthyl)-N-phenylamino]triphenylamine. The device had the following light emission characteristics, i.e., a light emission brightness of 280 (cd/m$^2$) at a direct current voltage of 5 V, a maximum light emission brightness of 32,000 (cd/m$^2$) and a light emission efficiency of 2.6 (lm/W).

Example 6

A solution of Compound (17) in chloroform was coated on a cleaned glass substrate with ITO electrode by a spin coating method, to form a hole-injecting layer having a thickness of 40 nm. Then, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above light-emitting layer was formed by vapor deposition under a vacuum of $10^{-6}$ Torr at a substrate temperature of room temperature. The device had the following light emission characteristics, i.e., a light emission brightness of 230 (cd/m$^2$) at a direct current voltage of 5 V, a maximum light emission brightness of 26,000 (cd/m$^2$) and a light emission efficiency of 2.5 (lm/W).

Examples 7–27

Compound shown in Table 1 was vacuum-deposited on a cleaned glass substrate with ITO electrode, to obtain a hole-injecting layer having a thickness of 40 nm. Then, 4,4'-bis[N-(1-naphthyl)-N-phenylamino]biphenyl was vacuum-deposited to obtain a hole-transporting layer having a thickness of 10 nm. Further, an aluminum tris(8-hydroxyquinolinate) complex was vacuum-deposited to form a light-emitting layer having a thickness of 50 nm, and further, a gallium bis(2-methyl-8-hydroxyguinolinate)(1-phenolate) complex was vacuum-deposited to form an electron-injecting layer having a thickness of 30 nm. And, an electrode having a thickness of 150 nm was formed thereon from an aluminun/lithium alloy having an aluminum/lithium mixing ratio of 25/1, to obtain an organic EL device. The above hole-injecting layer and the light-emitting layer were formed by vapor deposition under a vacuum of $10^{-6}$ Torr at a substrate temperature of room temperature. The device had light emission characteristics as shown in Table 3.

TABLE 3

| Example | Compound | Brightness (cd/m$^2$) | Maximum brightness (cd/m$^2$) | Light emission efficiency (1 m/W) |
|---|---|---|---|---|
| 7 | (1) | 310 | 25,000 | 2.6 |
| 8 | (2) | 300 | 26,000 | 2.5 |
| 9 | (3) | 320 | 28,000 | 3.0 |
| 10 | (4) | 310 | 29,000 | 2.2 |
| 11 | (5) | 290 | 28,000 | 2.0 |
| 12 | (6) | 250 | 23,000 | 2.1 |
| 13 | (7) | 260 | 25,000 | 2.2 |
| 14 | (8) | 230 | 26,000 | 2.3 |
| 15 | (9) | 250 | 29,000 | 2.8 |
| 16 | (10) | 210 | 28,000 | 2.6 |
| 17 | (11) | 230 | 24,000 | 2.0 |
| 18 | (12) | 230 | 22,000 | 2.1 |
| 19 | (13) | 250 | 26,000 | 2.4 |
| 20 | (14) | 250 | 24,000 | 2.2 |
| 21 | (15) | 220 | 21,000 | 2.0 |
| 22 | (16) | 200 | 20,000 | 1.9 |
| 23 | (17) | 180 | 18,000 | 1.6 |
| 24 | (18) | 150 | 15,000 | 1.7 |
| 25 | (19) | 190 | 20,000 | 1.9 |
| 26 | (20) | 200 | 21,000 | 2.1 |
| 27 | (21) | 230 | 25,000 | 2.5 |

Example 28

4,4'-bis[N-(1-naphthyl)-N-phenylamino]biphenyl was vacuum-deposited on a cleaned glass substrate with ITO electrode, to obtain a hole-injecting layer having a thickness of 40 nm. Then, Compound (6) was vacuum-deposited to obtain a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 480 (cd/m$^2$) at a direct current voltage of 5 V, a maximum light emission brightness of 27,000 (cd/m$^2$) and a light emission efficiency of 2.3 (lm/W).

Example 29

Compound (2) was vacuum-deposited on a cleaned glass substrate with ITO electrode, to obtain a hole-injecting layer having a thickness of 40 nm. Then, 4,4'-bis[N-(1-naphthyl)-N-phenylamino]biphenyl was vacuum-deposited to obtain a hole-transporting layer having a thickness of 10 nm. Further, N,N,N',N'-[4-(α,α'-dimethylbenzyl)phenyl]-anthranyl-9,10-diamine was vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 1,200 (cd/m$^2$) at a direct current voltage of 5 V, a maximum light emission brightness of 69,000 (cd/m$^2$) and a light emission efficiency of 5.2 (lm/W).

Example 30

An organic EL device was prepared in the same manner as in Example 29 except that a hole-injecting layer obtained by the vacuum deposition of Compound (2) was heated in a vacuum heating furnace at 65° C. for 3 hours. The device had the following light emission characteristics, i.e., a light emission brightness of 1,200 (cd/m$^2$) at a direct current voltage of 5 V, a maximum light emission brightness of 76,000 (cd/m$^2$) and a light emission efficiency of 5.9 (lm/W). The heating improved the device in the light emission characteristics. It is assumed that the improvement was made because the heating brought Compound (2) into an oriented state advantageous for the injection and transportation of holes.

Example 31

Compound (4) was vacuum-deposited on a cleaned glass substrate with ITO electrode, to obtain a hole-injecting layer having a thickness of 40 nm. Then, a Compound (21) and rubrene in a weight ratio of 10:1 were vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 680 (cd/m$^2$) at a direct current voltage of 5 V, a maximum light emission brightness of 47,000 (cd/m$^2$) and a light emission efficiency of 3.3 (lm/W).

Example 32

An organic EL device was prepared in the same manner as in Example 7 except that a light-emitting layer having a thickness of 40 nm was formed by vapor deposition of an aluminum tris(8-hydroxyguinolinate) complex and quinacridone in a weight ratio of 20:1. The device had the following light emission characteristics, i.e., a brightness of 600 (cd/m$^2$) at a direct current voltage of 5 V, a maximum light emission brightness of 40,000 (cd/m$^2$) and a light emission efficiency of 3.9 (lm/W).

Example 33

An organic EL device was prepared in the same manner as in Example 32 except that an electron-injecting layer having a thickness of 40 nm was formed by vapor deposition of Compound (20) in place of the aluminum tris(8-hydroxyquinolinate). The device had the following light emission characteristics, i.e., a light emission brightness of 600 (cd/m$^2$) at a direct current voltage of 5 V, a maximum light emission brightness of 42,000 (cd/m$^2$) and a light emission efficiency of 4.4 (lm/W).

Comparative Example 1

An organic EL device was prepared in the same manner as in Example 1 except that Compound (1) was replaced with 4,4',4"-tris[N-(3-methylphenyl)-N-phenylamino]triphenylamine. The device had the following light emission characteristics, i.e., a light emission brightness of about 160 (cd/m$^2$) at a direct current voltage of 5 V and a light emission efficiency of 1.2 (lm/W).

Example 34

Compound (22) was vacuum-deposited on a cleaned glass substrate with ITO electrode, to obtain a hole-injecting layer having a thickness of 30 nm. Then, an aluminum tris(8-hydroxyquinolinate) complex was vacuum-deposited to form a light-emitting layer having a thickness of 50 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of 10$^{-6}$ Torr at a substrate temperature of room temperature. The device had the following light emission characteristics, i.e., a light emission brightness of 110 (cd/m$^2$) at a direct current voltage of 5 V, a maximum light emission brightness of 18,000 (cd/m$^2$) and a light emission efficiency of 2.0 (lm/W).

Example 35

An organic EL device was prepared in the same manner as in Example 34 except that a hole-injecting layer was formed from a solution of Compound (26) in chloroform by a spin coating method. The device had the following light emission characteristics, i.e., a light emission brightness of 220 (cd/m$^2$) at a direct current voltage of 5 V, a maximum light emission brightness of 20,000 (cd/m$^2$) and a light emission efficiency of 2.1 (lm/W).

Example 36

Compound (27) was vacuum-deposited on a cleaned glass substrate with ITO electrode, to obtain a first hole-injecting layer having a thickness of 40 nm. Then, N,N'-diphenyl-N,N'-(3-methylphenyl)-1,1'-biphenyl-4,4'-diamine was vacuum-deposited to obtain a second hole-injecting layer having a thickness of 10 nm. Further, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of 10$^{-6}$ Torr at a substrate temperature of room temperature. The device had the following light emission characteristics, i.e., a light emission brightness of 260 (cd/m$^2$) at a direct current voltage of 5 V, a maximum light emission brightness of 26,000 (cd/m$^2$) and a light emission efficiency of 2.5 (lm/W).

Example 37

An organic EL device was prepared in the same manner as in Example 36 except that a second hole-injecting layer was formed from N,N'-(4-methylphenyl)-N,N'-(4-n-butylphenyl)-phenanthrene-9,10-diamine. The device had the following light emission characteristics, i.e., a light emission brightness of 280 (cd/m$^2$) at a direct current voltage of 5 V, a maximum light emission brightness of 28,000 (cd/m$^2$) and a light emission efficiency of 2.6 (lm/W).

Example 38

4,4',4"-tris[N-(1-naphthyl)-N-phenylamino]triphenylamine was vacuum-deposited on a cleaned glass substrate with ITO electrode, to obtain a first hole-injecting layer having a thickness of 40 nm. Then, Compound (23) was vacuum-deposited to obtain a second hole-injecting layer having a thickness of 10 nm. Further, an aluminum tris(8-hydroxyguinolinate) complex was vacuum-deposited to form a light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of 10$^{-6}$ Torr at a substrate temperature of room temperature. The device had the following light emission characteristics, i.e., a light emission brightness of 260 (cd/m$^2$) at a direct current voltage of 5 V, a maximum light emission brightness of 26,000 (cd/m$^2$) and a light emission efficiency of 2.5 (lm/W).

Example 39

A solution of Compound (48) in chloroform was coated on a cleaned glass substrate with ITO electrode by a spin coating method, to form a hole-injecting layer having a thickness of 40 nm. Then, an aluminum tris(8-hydroxyquinolinate) complex was vacuum-deposited to form a light-emitting layer having a thickness of 40 nm, and an electrode having a thickness of 150 nm was formed thereon from a magnesium/silver alloy having a magnesium/silver mixing ratio of 10/1, to obtain an organic EL device. The above light-emitting layer was formed by vapor deposition under a vacuum of 10$^{-6}$ Torr at a substrate temperature of room temperature. The device had the following light emission characteristics, i.e., a light emission brightness of 220 (cd/m$^2$) at a direct current voltage of 5 V, a maximum light emission brightness of 27,000 (cd/m$^2$) and a light emission efficiency of 2.6 (lm/W).

Examples 40–88

Compound shown in Table 4 was vacuum-deposited on a cleaned glass substrate with ITO electrode, to obtain a first hole-injecting layer having a thickness of 40 nm. Then, 4,4'-bis[N-(1-naphthyl)-N-phenylamino]biphenyl was vacuum-deposited to obtain a second hole-injecting layer having a thickness of 10 nm. Further, an aluminum tris(8-hydroxyquinolinate) complex was vacuum-deposited to form a light-emitting layer having a thickness of 50 nm, and further, a gallium bis(2-methyl-8-hydroxyquinolinate) phenolate complex was vacuum-deposited to form an electron-injecting layer having a thickness of 30 nm. And, an electrode having a thickness of 150 nm was formed thereon from an aluminun/lithium alloy having an aluminum/lithium mixing ratio of 25/1, to obtain an organic EL device. The above organic layers were formed by vapor deposition under a vacuum of $10^{-6}$ Torr at a substrate temperature of room temperature. The device had light emission characteristics as shown in Table 4.

Examples 89–104

4,4',4"-tris[N-(3-methylphenyl)-N-phenylamino]triphenylamine was vacuum-deposited on a cleaned glass substrate with ITO electrode, to obtain a first hole-injecting layer having a thickness of 40 nm. Then, Compound shown in Table 4 was vacuum-deposited to obtain a second hole-injecting layer having a thickness of 10 nm. Further, an aluminum tris(8-hydroxyquinolinate) complex was vacuum-deposited to form a light-emitting layer having a thickness of 50 nm, and further, a gallium bis(2-methyl-8-hydroxyquinolinate)phenolate complex was vacuum-deposited to form an electron-injecting layer having a thickness of 30 nm. And, an electrode having a thickness of 150 nm was formed thereon from an aluminun/lithium alloy having an aluminum/lithium mixing ratio of 25/1, to obtain an organic EL device. The above organic layers were formed by vapor deposition under a vacuum of $10^{-6}$ Torr at a substrate temperature of room temperature. The device had light emission characteristics as shown in Table 4.

TABLE 4

| Example | Compound | Brightness (cd/m$^2$) | Maximum brightness (cd/m$^2$) | Light emission efficiency (1 m/W) |
|---|---|---|---|---|
| 40 | (22) | 300 | 23,000 | 2.4 |
| 41 | (23) | 310 | 21,000 | 2.2 |
| 42 | (24) | 290 | 21,000 | 2.2 |
| 43 | (25) | 300 | 22,000 | 2.3 |
| 44 | (26) | 330 | 22,000 | 2.2 |
| 45 | (27) | 340 | 22,000 | 2.2 |
| 46 | (28) | 300 | 23,000 | 2.3 |
| 47 | (29) | 330 | 24,000 | 2.2 |
| 48 | (30) | 280 | 22,000 | 2.2 |
| 49 | (31) | 280 | 23,000 | 2.4 |
| 50 | (32) | 290 | 24,000 | 2.4 |
| 51 | (33) | 350 | 25,000 | 2.4 |
| 52 | (34) | 330 | 25,000 | 2.5 |
| 53 | (35) | 320 | 25,000 | 2.5 |
| 54 | (36) | 300 | 23,000 | 2.4 |
| 55 | (37) | 360 | 24,000 | 2.3 |
| 56 | (38) | 320 | 29,000 | 2.3 |
| 57 | (39) | 300 | 27,000 | 2.7 |
| 58 | (40) | 300 | 25,000 | 2.2 |
| 59 | (41) | 310 | 25,000 | 2.4 |
| 60 | (42) | 330 | 24,000 | 2.2 |
| 61 | (43) | 300 | 24,000 | 2.0 |
| 62 | (44) | 270 | 23,000 | 2.5 |
| 63 | (45) | 280 | 27,000 | 2.4 |
| 64 | (46) | 260 | 23,000 | 2.4 |
| 65 | (47) | 300 | 23,000 | 2.4 |
| 66 | (48) | 330 | 24,000 | 2.2 |
| 67 | (49) | 320 | 25,000 | 2.8 |
| 68 | (50) | 310 | 28,000 | 2.5 |
| 69 | (51) | 320 | 24,000 | 2.7 |
| 70 | (52) | 370 | 26,000 | 2.8 |
| 71 | (53) | 370 | 27,000 | 2.8 |
| 72 | (54) | 330 | 26,000 | 2.4 |
| 73 | (55) | 320 | 28,000 | 2.3 |
| 74 | (56) | 350 | 22,000 | 2.3 |
| 75 | (57) | 320 | 30,000 | 2.6 |
| 76 | (58) | 350 | 30,000 | 2.3 |
| 77 | (59) | 320 | 27,000 | 2.5 |
| 78 | (60) | 330 | 27,000 | 2.3 |
| 79 | (61) | 320 | 28,000 | 2.6 |
| 80 | (62) | 310 | 29,000 | 2.3 |
| 81 | (63) | 350 | 26,000 | 2.5 |
| 82 | (64) | 340 | 26,000 | 2.3 |
| 83 | (65) | 320 | 27,000 | 2.3 |
| 84 | (66) | 320 | 28,000 | 2.6 |
| 85 | (67) | 310 | 24,000 | 2.6 |
| 86 | (68) | 350 | 28,000 | 2.6 |
| 87 | (69) | 330 | 27,000 | 2.6 |
| 88 | (70) | 320 | 26,000 | 2.7 |
| 89 | (22) | 350 | 21,000 | 2.3 |
| 90 | (26) | 250 | 30,000 | 2.0 |
| 91 | (33) | 320 | 21,000 | 2.9 |
| 92 | (42) | 300 | 22,000 | 2.3 |
| 93 | (47) | 350 | 25,000 | 2.0 |
| 94 | (51) | 310 | 27,000 | 2.9 |
| 95 | (56) | 260 | 28,000 | 2.8 |
| 96 | (61) | 340 | 30,000 | 2.2 |
| 97 | (70) | 370 | 29,000 | 2.4 |
| 98 | (71) | 370 | 23,000 | 2.7 |
| 99 | (72) | 340 | 22,000 | 2.6 |
| 100 | (73) | 350 | 25,000 | 2.6 |
| 101 | (74) | 340 | 25,000 | 2.5 |
| 102 | (75) | 400 | 31,000 | 2.8 |
| 103 | (76) | 400 | 30,000 | 2.8 |
| 104 | (77) | 370 | 32,000 | 2.5 |

Brightness and light emission efficiency = values under direct current of 5 (V).

Example 105

Compound (48) was vacuum-deposited on a cleaned glass substrate with ITO electrode, to obtain a first hole-injecting layer having a thickness of 40 nm. Then, 4,4'-bis[N-(1-naphthyl)-N-phenylamino]biphenyl was vacuum-deposited to obtain a second hole-injecting layer having a thickness of 10 nm. Further, N,N,N',N'-[4-($\alpha,\alpha$'-dimethylbenzyl)phenyl]-anthranyl-9,10-diamine was vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 1,000 (cd/m$^2$) at a direct current voltage of 5 V, a maximum light emission brightness of 67,000 (cd/m$^2$) and a light emission efficiency of 4.7 (lm/W).

Example 106

An organic EL device was prepared in the same manner as in Example 65 except that a hole-injecting layer obtained by the vacuum deposition of Compound (48) was heated in a vacuum heating furnace at 65° C. for 3 hours. The device had the following light emission characteristics, i.e., a light emission brightness of 1,200 (cd/m$^2$) at a direct current voltage of 5 V, a maximum light emission brightness of 78,000 (cd/m$^2$) and a light emission efficiency of 5.9 (lm/W). The heating improved the device in the light emission characteristics. It is assumed that the improvement was made because the heating brought Compound (48) into an oriented state advantageous for the injection and transportation of holes.

Example 107

N,N'-diphenyl-N,N'-(3-methylphenyl)-1,1'-biphenyl-4,4'-diamine was vacuum-deposited on a cleaned glass substrate with ITO electrode, to obtain a hole-injecting layer having a thickness of 40 nm. Then, Compound (66) was vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 290 (cd/$m^2$) at a direct current voltage of 5 V, a maximum light emission brightness of 21,000 (cd/$m^2$) and a light emission efficiency of 2.7 (lm/W).

Example 108

Compound (46) was vacuum-deposited on a cleaned glass substrate with ITO electrode, to obtain a hole-injecting layer having a thickness of 50 nm. Then, Compound (35) was vacuum-deposited to obtain a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 140 (cd/$m^2$) at a direct current voltage of 5 V, a maximum light emission brightness of 25,000 (cd/$m^2$) and a light emission efficiency of 2.1 (lm/W).

Example 109

Compound (25) was vacuum-deposited on a cleaned glass substrate with ITO electrode, to obtain a hole-injecting layer having a thickness of 40 nm. Then, a Compound (38) and rubrene in a weight ratio of 100:3 were vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 630 (cd/$m^2$) at a direct current voltage of 5 V, a maximum light emission brightness of 44,000 (cd/$m^2$) and a light emission efficiency of 3.7 (lm/W).

Example 110

An organic EL device was prepared in the same manner as in Example 40 except that a light-emitting layer having a thickness of 40 nm was formed by vapor deposition of an aluminum tris(8-hydroxyquinolinate) complex and quinacridone in a weight ratio of 100:1. The device had the following light emission characteristics, i.e., a brightness of 590 (cd/$m^2$) at a direct current voltage of 5 V, a maximum light emission brightness of 38,000 (cd/$m^2$) and a light emission efficiency of 3.9 (lm/W).

Example 111

An organic EL device was prepared in the same manner as in Example 110 except that an electron-injecting layer having a thickness of 40 nm was formed by vapor deposition of Compound (63) in place of the gallium bis(2-methyl-8-hydroxyquinolinate)phenolate complex. The device had the following light emission characteristics, i.e., a light emission brightness of 610 (cd/$m^2$) at a direct current voltage of 5 V, a maximum light emission brightness of 42,000 (cd/$m^2$) and a light emission efficiency of 4.4 (lm/W).

Example 112

4,4'-bis[N-(1-naphthyl)-N-phenylamino]biphenyl was vacuum-deposited on a cleaned glass substrate with ITO electrode, to obtain a hole-injecting layer having a thickness of 30 nm. Then, a Compound (40) and quinacridone in a weight ratio of 50:1 were vacuum-deposited to form a light-emitting layer having a thickness of 50 nm. Further, a gallium bis(2-methyl-8-hydroxyquinolate)(1-naphtholate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 540 (cd/$m^2$) at a direct current voltage of 5 V, a maximum light emission brightness of 35,000 (cd/$m^2$) and a light emission efficiency of 3.6 (lm/W).

Example 113

4,4'-bis[N-(1-naphthyl)-N-phenylamino]biphenyl was vacuum-deposited on a cleaned glass substrate with ITO electrode, to obtain a hole-injecting layer having a thickness of 30 nm. Then, a Compound (40) and N,N'-diethylquinacridone in a weight ratio of 20:1 were vacuum-deposited to form a light-emitting layer having a thickness of 50 nm. Further, a gallium bis(2-methyl-8-hydroxyguinolate)(1-naphtholate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 490 (cd/$m^2$) at a direct current voltage of 5 V, a maximum light emission brightness of 42,000 (cd/$m^2$) and a light emission efficiency of 4.5 (lm/W).

Example 114

4,4',4"-tris[N-(3-methylphenyl)-N-phenylamino]triphenylamine was vacuum-deposited on a cleaned glass substrate with ITO electrode, to obtain a hole-injecting layer having a thickness of 40 nm. Then, a Compound (38) and diphenylanthracene in a weight ratio of 100:3 were vacuum-deposited to form a light-emitting layer having a thickness of 50 nm. Further, a zinc bis(o-(2-benzothiazolyl)phenolate complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above organic layers were formed by vapor deposition under a vacuum of $10^{-6}$ Torr at a substrate temperature of room temperature. The device had the following light emission characteristics, i.e., a light emission brightness of 220 (cd/$m^2$) at a direct current voltage of 5 V, a maximum light emission brightness of 26,000 (cd/$m^2$) and a light emission efficiency of 2.9 (lm/W).

Examples 115–121

An organic EL device was prepared in the same manner as in Example 89 except that Compound (22) was replaced with Compound shown in Table 5. Table 5 shows the light emission characteristics.

TABLE 5

| Example | Compound | Brightness (cd/$m^2$) | Maximum brightness (cd/$m^2$) | Light emission efficiency (1 m/W) |
|---------|----------|-----------------------|-------------------------------|-----------------------------------|
| 115 | (71) | 370 | 23,000 | 2.7 |
| 116 | (72) | 340 | 22,000 | 2.6 |
| 117 | (73) | 360 | 25,000 | 2.6 |
| 118 | (74) | 340 | 25,000 | 2.5 |
| 119 | (75) | 400 | 31,000 | 2.8 |
| 120 | (76) | 400 | 30,000 | 2.8 |
| 121 | (77) | 370 | 32,000 | 2.5 |

Comparative Example 2

An organic EL device was prepared in the same manner as in Example 105 except that Compound (48) was replaced with 4,4',4"-tris[N-(3-methylphenyl)-N-phenylamino] triphenylamine. The device had the following light emission characteristics, i.e., a light emission brightness of about 550 (cd/$m^2$) at a direct current voltage of 5 V and a light emission efficiency of 3.5 (lm/W).

Comparative Example 3

An organic EL device was prepared in the same manner as in Example 38 except that Compound (23) was replaced with 4,4'-bis[N-(1-naphthyl)-N-phenylamino]biphenyl. The device had the following light emission characteristics, i.e., a light emission brightness of about 150 (cd/$m^2$) at a direct current voltage of 5 V and a light emission efficiency of 1.4 (lm/W).

Comparative Example 4

An organic EL device was prepared in the same manner as in Example 109 except that Compound (59) was replaced with 4,4'-bis[N-(1-naphthyl)-N-phenylamino]biphenyl. The device had the following light emission characteristics, i.e., a light emission brightness of about 20 (cd/$m^2$) at a direct current voltage of 5 V and a light emission efficiency of 2.2 (lm/W).

Example 122

Compound (78) was vacuum-deposited on a cleaned glass substrate with ITO electrode, to obtain a hole-injecting layer having a thickness of 30 nm. Then, an aluminum tris(8-hydroxyquinolinate) complex was vacuum-deposited to form a light-emitting layer having a thickness of 50 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of $10^{-6}$ Torr at a substrate temperature of room temperature. The device had the following light emission characteristics, i.e., a light emission brightness of 120 (cd/$m^2$) at a direct current voltage of 5 V, a maximum light emission brightness of 16,000 (cd/$m^2$) and a light emission efficiency of 1.8 (lm/W).

Example 123

An organic EL device was prepared in the same manner as in Example 122 except that a hole-injecting layer was formed from a solution of Compound (80) in chloroform by a spin coating method. The device had the following light emission characteristics, i.e., a light emission brightness of 150 (cd/$m^2$) at a direct current voltage of 5 V, a maximum light emission brightness of 12,000 (cd/$m^2$) and a light emission efficiency of 1.8 (lm/W).

Example 124

Compound (81) was vacuum-deposited on a cleaned glass substrate with ITO electrode, to obtain a hole-injecting layer having a thickness of 40 nm. Then, N,N'-diphenyl-N,N'-(3-methylphenyl)-1,1'-biphenyl-4,4'-diamine was vacuum-deposited to obtain a second hole-injecting layer having a thickness of 10 nm. Further, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of $10^{-6}$ Torr at a substrate temperature of room temperature. The device had the following light emission characteristics, i.e., a light emission brightness of 140 (cd/$m^2$) at a direct current voltage of 5 V, a maximum light emission brightness of 21,000 (cd/$m^2$) and a light emission efficiency of 2.1 (lm/W).

Example 125

4,4',4"-tris[N-(3-methylphenyl)-N-phenylamino] triphenylamine was vacuum-deposited on a cleaned glass substrate with ITO electrode, to obtain a hole-injecting layer having a thickness of 40 nm. Then, a Compound (80) was vacuum-deposited to form a second hole-injecting layer having a thickness of 10 nm. Further, an aluminum tris(8-hydroxyquinolinate) complex was vacuum-deposited to form an electron injection type light-emitting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layers and the light-emitting layer were formed by vapor deposition under a vacuum of $10^{-6}$ Torr at a substrate temperature of room temperature. The device had the following light emission characteristics, i.e., a light emission brightness of 250 (cd/$m^2$) at a direct current voltage of 5 V, a maximum light emission brightness of 28,000 (cd/$m^2$) and a light emission efficiency of 2.5 (lm/W).

Example 126

An organic EL device was prepared in the same manner as in Example 125 except that the 4,4',4"-tris[N-(3-methylphenyl)-N-phenylamino]triphenylamine was replaced with 4,4',4"-tris[N-(1-naphthyl)-N-phenylamino]triphenylamine. The device had the following light emission characteristics, i.e., a light emission brightness of 250 (cd/m$^2$) at a direct current voltage of 5 V, a maximum light emission brightness of 22,000 (cd/m$^2$) and a light emission efficiency of 2.2 (lm/W).

Example 127

A solution of Compound (94) in chloroform was coated on a cleaned glass substrate with ITO electrode by a spin coating method, to form a hole-injecting layer having a thickness of 40 nm. Then, an aluminum tris(8-hydroxyquinolinate) complex was vacuum-deposited to form an electron injection type light-emitting layer having a thickness of 40 nm, and an electrode having a thickness of 100 nm was formed thereon from a magnesium/silver alloy having a magnesium/silver mixing ratio of 10/1, to obtain an organic EL device. The above light-emitting layer was formed by vapor deposition under a vacuum of 10$^{-6}$ Torr at a substrate temperature of room temperature. The device had the following light emission characteristics, i.e., a light emission brightness of 200 (cd/m$^2$) at a direct current voltage of 5 V, a maximum light emission brightness of 19,000 (cd/m$^2$) and a light emission efficiency of 1.7 (lm/W).

Examples 128–148

Compound shown in Table 6 was vacuum-deposited on a cleaned glass substrate with ITO electrode, to obtain a hole-injecting layer having a thickness of 40 nm. Then, 4,4'-bis[N-(1-naphthyl)-N-phenylamino]biphenyl was vacuum-deposited to obtain a hole-transporting layer having a thickness of 10 nm. Further, an aluminum tris(8-hydroxyquinolinate) complex was vacuum-deposited to form a light-emitting layer having a thickness of 50 nm, and further, a gallium bis(2-methyl-8-hydroxyquinolinate) phenolate complex was vacuum-deposited to form an electron-injecting layer having a thickness of 30 nm. And, an electrode having a thickness of 150 nm was formed thereon from an aluminun/lithium alloy having an aluminum/lithium mixing ratio of 25/1, to obtain an organic EL device. The above hole-injecting layer and the above light-emitting layer were formed by vapor deposition under a vacuum of 10$^{-6}$ Torr at a substrate temperature of room temperature. The device had light emission characteristics as shown in Table 6.

TABLE 6

| Example | Compound | Brightness (cd/m$^2$) | Maximum brightness (cd/m$^2$) | Light emission efficiency (1 m/W) |
|---|---|---|---|---|
| 128 | (78) | 280 | 29,000 | 2.4 |
| 129 | (79) | 290 | 27,000 | 2.3 |
| 130 | (80) | 300 | 24,000 | 2.0 |
| 131 | (81) | 290 | 27,000 | 2.4 |
| 132 | (82) | 280 | 21,000 | 1.4 |
| 133 | (83) | 250 | 20,000 | 1.8 |
| 134 | (84) | 250 | 21,000 | 2.0 |
| 135 | (85) | 240 | 15,000 | 1.3 |
| 136 | (86) | 290 | 19,000 | 1.8 |
| 137 | (87) | 310 | 13,000 | 1.6 |
| 138 | (88) | 200 | 23,000 | 1.9 |
| 139 | (89) | 360 | 27,000 | 2.5 |
| 140 | (90) | 290 | 30,000 | 2.8 |
| 141 | (91) | 150 | 19,000 | 1.7 |
| 142 | (92) | 200 | 20,000 | 1.8 |
| 143 | (93) | 230 | 28,000 | 2.6 |

TABLE 6-continued

| Example | Compound | Brightness (cd/m$^2$) | Maximum brightness (cd/m$^2$) | Light emission efficiency (1 m/W) |
|---|---|---|---|---|
| 144 | (94) | 290 | 19,000 | 1.6 |
| 145 | (95) | 180 | 14,000 | 1.1 |
| 146 | (96) | 170 | 23,000 | 1.9 |
| 147 | (97) | 260 | 20,000 | 1.5 |
| 148 | (98) | 270 | 24,000 | 2.0 |

Example 149

4,4'-bis[N-(1-naphthyl)-N-phenylamino]biphenyl was vacuum-deposited on a cleaned glass substrate with ITO electrode, to obtain a hole-injecting layer having a thickness of 40 nm. Then, a Compound (82) was vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of 10$^{-6}$ Torr at a substrate temperature of room temperature. The device had the following light emission characteristics, i.e., a light emission brightness of 380 (cd/m$^2$) at a direct current voltage of 5 V, a maximum light emission brightness of 26,000 (cd/m$^2$) and a light emission efficiency of 2.1 (lm/W).

Example 150

Compound (78) was vacuum-deposited on a cleaned glass substrate with ITO electrode, to obtain a hole-injecting layer having a thickness of 40 nm. Then, 4,4'-bis[N-(1-naphthyl)-N-phenylamino]biphenyl was vacuum-deposited to obtain a hole-transporting layer having a thickness of 10 nm. Further, N,N,N',N'-[4-(α,α'-dimethylbenzyl)phenyl]-anthranyl-9,10-diamine was vacuum-deposited to form a light-emitting layer having a thickness of 50 nm. Further, an aluminum tris(8-hydroxyquinolinate) complex was vacuum-deposited to form an electron-injecting layer having a thickness of 40 nm, and an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of 10$^{-6}$ Torr at a substrate temperature of room temperature. The device had the following light emission characteristics, i.e., a light emission brightness of 1,000 (cd/m$^2$) at a direct current voltage of 5 V, a maximum light emission brightness of 59,000 (cd/m$^2$) and a light emission efficiency of 5.0 (lm/W).

Example 151

An organic EL device was prepared in the same manner as in Example 150 except that a hole-injecting layer obtained by the vacuum deposition of Compound (79) was heated in a vacuum heating furnace at 65° C. for 3 hours.

The device had the following light emission characteristics, i.e., a light emission brightness of 1,100 (cd/m$^2$) at a direct current voltage of 5 V, a maximum light emission brightness of 56,000 (cd/m$^2$) and a light emission efficiency of 4.9 (lm/W). The heating improved the device in the light emission characteristics. It is assumed that the improvement was made because the heating brought Compound (79) into an oriented state advantageous for the injection and transportation of holes.

Example 152

Compound (81) was vacuum-deposited on a cleaned glass substrate with ITO electrode, to obtain a hole-injecting layer having a thickness of 40 nm. Then, a Compound (97) and rubrene in a weight ratio of 10:1 were vacuum-deposited to form a light-emitting layer having a thickness of 50 nm. Further, an aluminum tris(8-hyiroxyquinolinate) complex was vacuum-deposited to form an electron-injecting layer having a thickness of 40 nm, arid an electrode having a thickness of 150 nm was formed thereon from a magnesium/silver alloy having a magnesium/silver mixing ratio of 10/1, to obtain an organic EL device. The above hole-injecting layer and the light-emitting layer were formed by vapor deposition under a vacuum of 10$^{-6}$ Torr at a substrate temperature of room temperature. The device had the following light emission characteristics, i.e., a light emission brightness of 580 (cd/m$^2$) at a direct current voltage of 5 V, a maximum light emission brightness of 42,000 (cd/m$^2$) and a light emission efficiency of 2.8 (lm/W).

Example 153

An organic EL device was prepared in the same mariner as in Example 128 except that a light-emitting layer having a thickness of 40 nm was formed by vapor deposition of an aluminum tris(8-hydroxyquinolinate) complex and quinacridone in a weight ratio of 20:1. The device had the following light emission characteristics, i.e., a brightness of 520 (cd/m$^2$) at a direct current voltage of 5 V, a maximum light emission brightness of 32,000 (cd/m$^2$) and a light emission efficiency of 2.9 (lm/W).

Example 154

An organic EL device was prepared in the same manner as in Example 153 except that the aluminum tris(8-hydroxyquinolinate) complex was replaced with Compound (97) to obtain an electron-injecting layer having a thickness of 40 nm. The device had the following light emission characteristics, i.e., a brightness of 520 (cd/m$^2$) at a direct current voltage of 5 V, a maximum light emission brightness of 46,000 (cd/m$^2$) and a light emission efficiency of 3.4 (lm/W).

When the organic EL devices obtained in the above Examples were allowed to continuously emit light at 3 (mA/cm$^2$), all the organic EL devices emitted light with a brightness of more than 50% of the initial brightness value for more than 1,000 hours. When the organic EL devices obtained in Comparative Examples were allowed to continuously emit light under the same conditions, the light emission brightness of all the organic EL devices decreased to less than 50% of the initial brightness value in 200 hours, and the number of dark spots, which are portions emitting no light, increased. The reason therefor is as follows. The material of the present invention is a non-planar compound, and is therefore capable of forming an amorphous thin film. The material of the present invention exhibits improved capability of injecting holes, and the organic EL device exhibits improved capability of injecting holes, owing to a triphenylene ring in the compound. Further, since the organic EL device is improved in heat resistance, the organic EL device is improved in durability against heat generated during continuous emission of light, the capability of injection of holes from the electrode and adhesion to the substrate. Further, when the material of the present invention is used as an electron-injecting material, it can form an amorphous thin film. Since the material of the present invention (compounds of the formulae (I), (II) and (III)) contains many fused aromatic rings and has electron-attracting groups, it improves the capability of injecting electrons, and the organic EL device is therefore improved in the capability of injecting electrons. Further, the material of the present invention exhibits effective properties as a light-emitting material.

What is claimed is:

1. An organic electroluminescence device obtained by forming either a light-emitting layer or a plurality of organic compound thin layers including the light-emitting layer between a pair of electrodes composed of a cathode and an anode, wherein at least one layer contains a compound having the formula (I), (II) or (III),

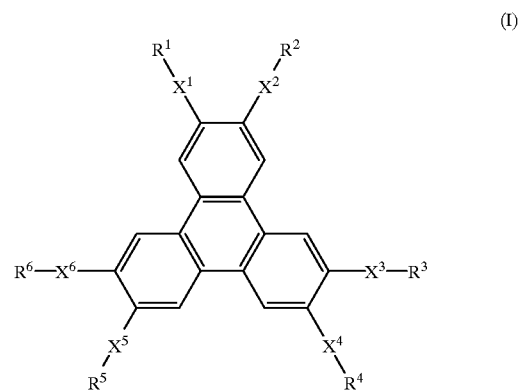

(I)

wherein each of R$^1$ to R$^6$ is independently a non-substituted methyl or ethyl group, a substituted methyl or ethyl group, and each of X$^1$ to X$^6$ is independently an oxygen atom or a sulfur atom, or each of X$^1$ to X$^6$ is independently a nitrogen atom to which a hydrogen atom, methyl group or ethyl group is bonded, (II)

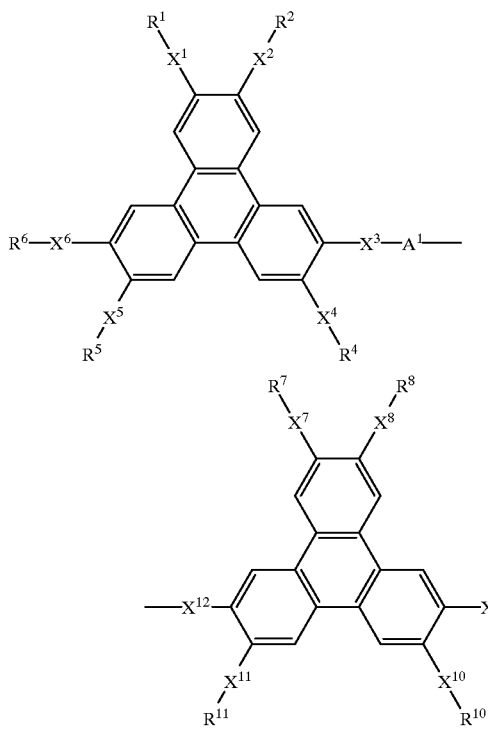

wherein each of $R^1$, $R^2$ and $R^4$ to $R^{11}$ is independently a non-substituted methyl or ethyl group, a substituted methyl or ethyl group, each of $X^1$ to $X^{11}$ is independently an oxygen atom, a sulfur atom or a nitrogen atom to which a hydrogen atom, methyl group or ethyl group is bonded, and $A^1$ is a chemically rational organic residue which is composed of C, H and O, or is composed of C, H, O and S, and has a molecular weight of 500 or less, (III)

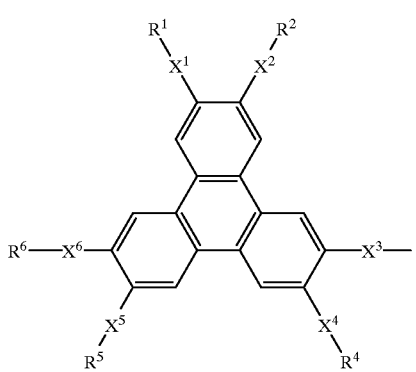

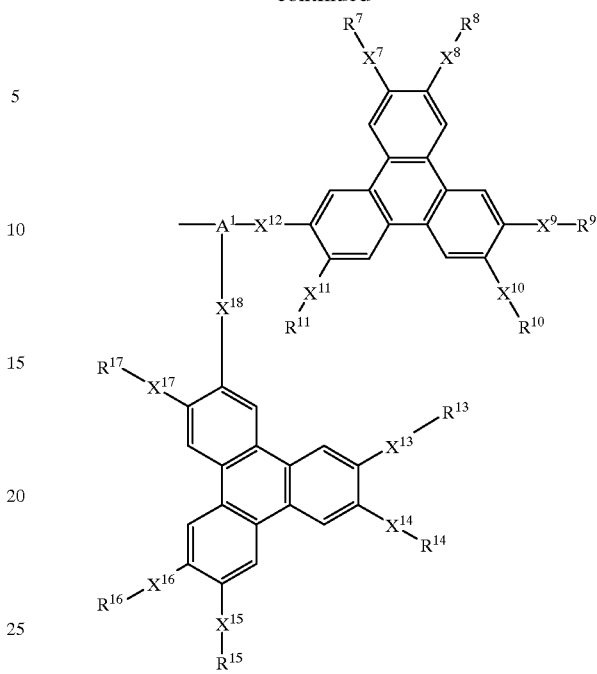

wherein each of $R^1$, $R^2$, $R^4$ to $R^{11}$ and $R^{13}$ to $R^{17}$ is independently a non-substituted methyl or ethyl group, a substituted methyl or ethyl group, each of $X^1$ to $X^{18}$ is independently an oxygen atom, a sulfur atom or a nitrogen atom to which a hydrogen atom, methyl group or ethyl group is bonded, and $A^2$ is a chemically rational organic residue which is composed of C, H and O, or is composed of C, H, O and S, and has a molecular weight of 500 or less, the thickness of each layer being in the range of from 10 nm to 0.2 μm.

2. The device according to claim 1, wherein the compound having the formula [I], [II] or [III] is a hole-transporting material.

3. The device according to claim 1, wherein the compound is the compound of the formula [I].

4. The device according to claim 3, wherein each of $X^1$ to $X^6$ is an oxygen atom.

5. The device according to claim 1, wherein the layer containing the compound is a hole-injecting layer formed between the anode and the light-emitting layer.

6. The device according to claim 1, wherein the layer containing the compound is the light-emitting layer.

7. The device according to claim 1, wherein a plurality of organic compound thin layers including the light-emitting layer are formed and the light-emitting layer and at least one other layer contain the compound.

8. The device according to claim 1, wherein the layer containing the compound further contains an organic fluorescent dyestuff.

* * * * *